US011072633B2

(12) United States Patent
Sampson et al.

(10) Patent No.: US 11,072,633 B2
(45) Date of Patent: Jul. 27, 2021

(54) AZASTEROIDS FOR TREATMENT OF TUBERCULOSIS

(71) Applicant: The Research Foundation for the State University of New York, Albany, NY (US)

(72) Inventors: Nicole Sampson, Setauket, NY (US); Xinxin Yang, Coram, NY (US); Tianao Yuan, Coram, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 16/097,558

(22) PCT Filed: Apr. 28, 2017

(86) PCT No.: PCT/US2017/030166
§ 371 (c)(1),
(2) Date: Oct. 29, 2018

(87) PCT Pub. No.: WO2017/190034
PCT Pub. Date: Nov. 2, 2017

(65) Prior Publication Data
US 2019/0161514 A1 May 30, 2019

Related U.S. Application Data

(60) Provisional application No. 62/329,634, filed on Apr. 29, 2016.

(51) Int. Cl.
C07J 73/00 (2006.01)
A61K 45/06 (2006.01)
A61P 31/06 (2006.01)
A61K 31/58 (2006.01)

(52) U.S. Cl.
CPC ............. *C07J 73/005* (2013.01); *A61K 31/58* (2013.01); *A61K 45/06* (2013.01); *A61P 31/06* (2018.01)

(58) Field of Classification Search
CPC ...................................................... C07J 73/00
USPC ............................................. 546/61; 514/284
See application file for complete search history.

(56) References Cited

FOREIGN PATENT DOCUMENTS

| UA | 76005 C2 | 1/2006 |
|---|---|---|
| WO | WO 1993/013124 A1 | 7/1993 |
| WO | WO 1993/013124 A1 | 7/1994 |
| WO | WO 2008/070039 A2 | 6/2008 |

OTHER PUBLICATIONS

Banker et al., Prodrugs, Modern Pharmaceutics, 3rd edition, Revised and Expanded, pp. 451 and 596.*
Jordan "Tamoxifen . . . " Nature Rev. v.2, p. 205-213 (20031.*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burger's Medicinal Chemistry and Drug Discovery. 5th ed. vol. 1: Principles and Practice, pp. 949-982, 1996.*
Bundgaard, Design of Prodrugs, Chapter 1, p. 1, 1985.*
Silverman, Prodrugs and Drug Delivery Systems, The Organic Chemistry of Drug Design and Drug action, Chapter 8, pp. 352-400, 1992.*
Thomas S.T. et al., "Inhibition of the *M. tuberculosis* 3 β-hydroxysteroid dehydrogenase by azasteroids". Bioorganic & Medicinal Chemistry Letters, 2011, V01. 21, No. 8, p. 2216-2219.
Frye S.V. et al., "6-Azasteroids: Potent Dual inhibitors of Human Type 1 and 2 Steroids 5 α-Reductase". Journal of medicinal chemistry, 1993, vol. 36, No. 6, p. 4313-4315.
Frye S.V. et al., "Structure-Activity Relationships for Inhibition of Type 1 and 2 Human 5 α-Reductase and Human Adrenal 3 β-Hydroxy-Δ5-steroids Isomerase by 6-Azaandrost-4-en-3-ones: Optimization of the C17 Substituent". Journal of medicinal chemistry, 1995, vol. 28, No. 14, p. 2621-2627.
Frye S.V. et al., "6-Azasteroids: Structure-Activity Relationships for Inhibition of Type 1 and 2 Human 5α-Reductase and Human Adrenal 3 β-Hydroxy-Δ$^5$-steroids Dehydrogenase/3-Keto-Δ$^5$-steroid Isomerase". Journal of medicinal chemistry, 1994, vol. 37, No. 15, p. 2352-2360.

(Continued)

*Primary Examiner* — Patricia L Morris
(74) *Attorney, Agent, or Firm* — Gary J. Gershik

(57) ABSTRACT

The present invention provides a compound having the structure:

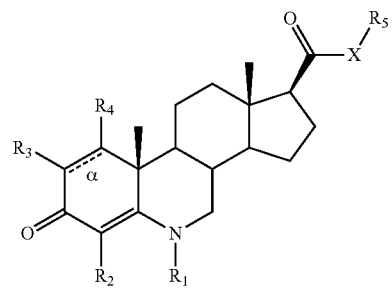

for use in combination with an anti-tuberculosis drug for treating a subject infected with *M. tuberculosis*.

19 Claims, 3 Drawing Sheets

(56) References Cited

OTHER PUBLICATIONS

Bakken G. A. et al., "QSARs for 6-Azasteroids as Inhibitiros of Human Type 1 5α-Reductase: Prediction of Binding Affinity and Selectivity Relative to 3-BHSD". Journal of chemical information and computer sciences. 2001, vol. 41, No, 5, p. 1255-1265.
Girones X. et al., "Molecular quantum similarity-based QSARs for binding affinities of several steroid sets". Journal of chemistry information and computer sciences, 2002, vol. 42, No. 5, p. 1185-1193.
Database Registry [online] RN 757916-64-6, entered STN Oct. 6, 2004, Retrieved from STN.
Database Registry [online] RN 1026032-70-1, entered STN Jun. 6, 2008, Retrieved from STN.
Database Registry [online] RN 1026196-20-2, entered STN Jun. 8, 2008, Retrieved from STN.
Database Registry [online] RN 1026361-55-6, entered STN Jun. 8, 2008, Retrieved from STN.
Database Registry [online] RN 1026862-76-9, entered STN Jun. 10, 2008, Retrieved from STN.
Database Registry [online] RN 1027970-78-0, entered STN Jun. 13, 2008, Retrieved from STN.
Database Registry [online] RN 1223090-38-7, entered STN May 13, 2010, Retrieved from STN.
Database Registry [online] RN 1223099-17-9, entered STN May 13, 2010, Retrieved from STN.
Database Registry [online] RN 1223100-25-1, entered STN May 13, 2010, Retrieved from STN.
Database Registry [online] RN 1350097-93-6, entered STN Dec. 7, 2011, Retrieved from STN.
Written Opinion of the International Searching Authority dated Sep. 7, 2017 in connection with PCT International Application No. PCT/US2017/030166.
International Search Report dated Sep. 7, 2017 in connection with PCT International Application No. PCT/US2017/030166.

\* cited by examiner

AZASTEROIDS FOR TREATMENT OF TUBERCULOSIS

CROSS-REFERENCE TO RELATED APPLICATIONS

This application is a § 371 national stage of PCT International Application No. PCT/US2017/030166, filed Apr. 28, 2017 and claims priority of U.S. Provisional Application No. 62/329,634, filed Apr. 29, 2016, the entire contents of each of which are hereby incorporated by reference into the application.

GOVERNMENT SUPPORT

This invention was made with government support under grant numbers AI092455 and HL127522, and contract number HHSN272201100009I, awarded by the National Institutes of Health. The government has certain rights in the invention.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

One third of the world's population carries the infectious agent that causes tuberculosis (TB), and every 21 seconds someone dies of TB worldwide. Current treatments for TB disease are not straightforward. The drug regimens must be of long duration to effectively cure TB disease. The drug treatments require daily patient monitoring and have many associated toxicities that are compounded by the high doses of long duration required.

TB treatment regimens for drug-sensitive TB require the use of multiple chemotherapeutics over a 2-month intensive therapy period utilizing isoniazid, rifampicin, pyrazinamide and ethambutol or streptomycin, followed by a continuation phase of 4 months of treatment with isoniazid and rifampicin. As a result of the arduous and difficult to follow regimen for TB treatment, there were approximately 480,000 cases of multi-drug resistant TB (MDR-TB) in 2014 of which about 15% develop into extensively-drug resistant TB (XDR-TB), which has been found in 100 countries (Raviglione, M. C. et al. 2007; NIAID Research Agenda 2007; Editorial 2006; Rattan, A. et al. 1998).

Totally-drug resistant TB (TDR-TB) has been reported recently in three countries (Suen, S. et al. 2014). Multi-drug resistant TB is defined as resistant to at least isoniazid and rifampicin, the two best first line drugs. Multi-drug resistant TB requires treatment for two years with a cocktail of at least 5 drugs. These second-line drugs tend to be more expensive, more toxic, and less effective drugs, and include ethionamide, cycloserine, moxifloxacin, as well as pyrazinamide, streptomycin and ethambutol. The precise combination depends on the patient history and drug sensitivity screening, as well as the country-specific protocols that depend on drug pricing and availability. All the regimens include daily injectables for up to 6 months. Monitoring these treatments to ensure compliance has a payer burden. Moreover MDR-TB treatment often requires hospitalization, and ideally, isolation. XDR-TB is typically treated with extremely toxic, last resort antibiotics and surgical removal of infected tissue.

The estimated 3 billion people with asymptomatic (latent) TB infections further confound reduction of TB incidence. They serve as an immense reservoir of infection, and their infections may be refractory due to the metabolic state of *Mycobacterium tuberculosis* (Mtb) (Russell, D. G. et al. 2009; Wakamoto, Y. et al. 2013; Murima, P. et al. 2014). Current CDC-recommended treatment is 12 weeks of once/week isoniazid and rifapentine (CDC 2010). Thus, the simplest TB treatment, which is for infected, asymptomatic patients, still requires 3 months of combination therapy antibiotic treatment.

New therapeutic agents with different mechanisms of action are needed to combat the spread of multi-drug, extensively-drug, and totally-drug resistant strains. Shortened treatment times and lower toxicities are required to increase the level of compliance with drug treatment regimens thereby minimizing the development of further drug resistance, and reducing payer cost. New therapeutic agents or combinations of agents are needed to treat latent TB in order to reduce the potential for future disease occurrence. TB disease affects people's lives during the years in which they contribute most to the economic viability of their families and their countries. The world's poorest countries are hardest hit by TB disease, with 94 percent of all TB cases occurring in these countries. It is estimated that over the next 10 years, developing countries will lose $1 to $3 trillion of productivity (TB Alliance 2015). Thus, there is a major incentive for governments and foundations to help fund the cost of developing improved anti-TB therapies.

SUMMARY OF THE INVENTION

The present invention also provides a compound having the structure:

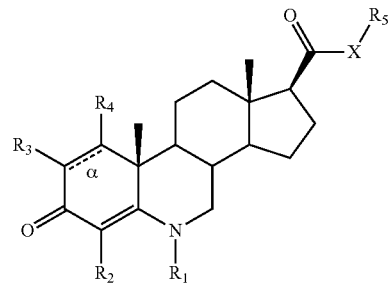

wherein
α is absent or present and when present is a bond,
  wherein when $R_3$ and $R_4$ combine to form a cycloalkyl group, then α is absent;
X is —NH—, —NH—NH—, —NH—C(O)—, —NH—C(S)—, —NH—NHC(O)— or —NH—NHC(S)—;
$R_1$ is —H, alkyl, alkenyl, alkynyl, aryl, heteroaryl, C(O)-alkyl, C(O)-haloalkyl, C(O)-cycloalkyl, C(O)-alkenyl, C(O)-alkynyl, C(O)-aryl, C(O)-heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, $SO_2$-alkyl, $SO_2$-haloalkyl, $SO_2$-cycloalkyl, $SO_2$-alkenyl, $SO_2$-alkynyl, $SO_2$-aryl, $SO_2$-heteroaryl or L-(anti-tuberculosis drug);
$R_2$ is H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-N(alkyl)$_2$;

$R_3$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-N(alkyl)$_2$, and $R_4$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, or alkyl-N(alkyl)$_2$, or $R_3$ and $R_4$ combine to form a cycloalkyl group;

$R_5$ is a substituted aryl, substituted heteroaryl, alkylaryl or L-(anti-tuberculosis drug), wherein L is a chemical linker comprising a functional group capable of forming a bond with an anti-tuberculosis drug;

wherein when α is absent, X is NH, and $R_1$, $R_2$, $R_3$ and $R_4$ are each H, then $R_5$ is other than 2-(tert-butyl)-5-(trifluoromethyl)phenyl, 2,5-di-tert-butylphenyl, 4-morpholinophenyl or 2-benzoylphenyl, or a salt or ester thereof.

The present invention also provides a method of treating a subject infected with *M. tuberculosis* comprising administering to the subject an amount of the compound having the structure:

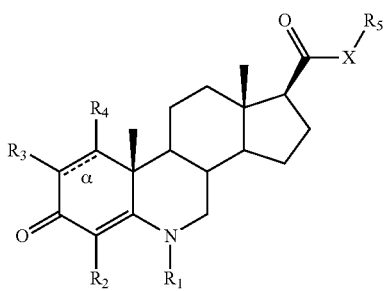

wherein

α is absent or present and when present is a bond, wherein when $R_3$ and $R_4$ combine to form a cycloalkyl group, then α is absent;

X is —NH—, —NH—NH—, —NH—C(O)—, —NH—C(S)—, —NH—NHC(O)— or —NH—NHC(S)—;

$R_1$ is —H, alkyl, alkenyl, alkynyl, aryl, heteroaryl, C(O)-alkyl, C(O)-haloalkyl, C(O)-cycloalkyl, C(O)-alkenyl, C(O)-alkynyl, C(O)-aryl, C(O)-heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, $SO_2$-alkyl, $SO_2$-haloalkyl, $SO_2$-cycloalkyl, $SO_2$-alkenyl, $SO_2$-alkynyl, $SO_2$-aryl, $SO_2$-heteroaryl or L-(anti-tuberculosis drug);

$R_2$ is H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-N(alkyl)$_2$;

$R_3$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-N(alkyl)$_2$, and $R_4$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, or alkyl-N(alkyl)$_2$, or $R_3$ and $R_4$ combine to form a cycloalkyl group;

$R_5$ is substituted aryl, substituted heteroaryl or alkylaryl, wherein when α is absent, X is NH, and $R_1$, $R_2$, $R_3$ and $R_4$ are each H, then $R_5$ is other than 3-tert-butylphenyl, 4-morpholinophenyl, 2-benzoylphenyl or 2,5-trifluoromethylphenyl, when α is absent, X is NH, $R_1$ is H or Boc, and $R_2$, $R_3$ and $R_4$ are each H, then $R_5$ is other than 2-trifluoromethoxy-4-halophenyl, 6-(5-fluoro-indol-1-yl)-2-(trifluoromethoxy)pyridin-3-yl or 2-trifluoromethoxy-3-trifluoromethylphenyl, and when α is absent, X is —NH—C(S)—, and $R_1$, $R_2$, $R_3$ and $R_4$ are each H, then $R_5$ is other than 2-ethylpyridin-4-yl, or a salt or ester thereof, in combination with an anti-tuberculosis drug, so as to thereby treat the subject.

DETAILED DESCRIPTION OF THE INVENTION

Figure 1:
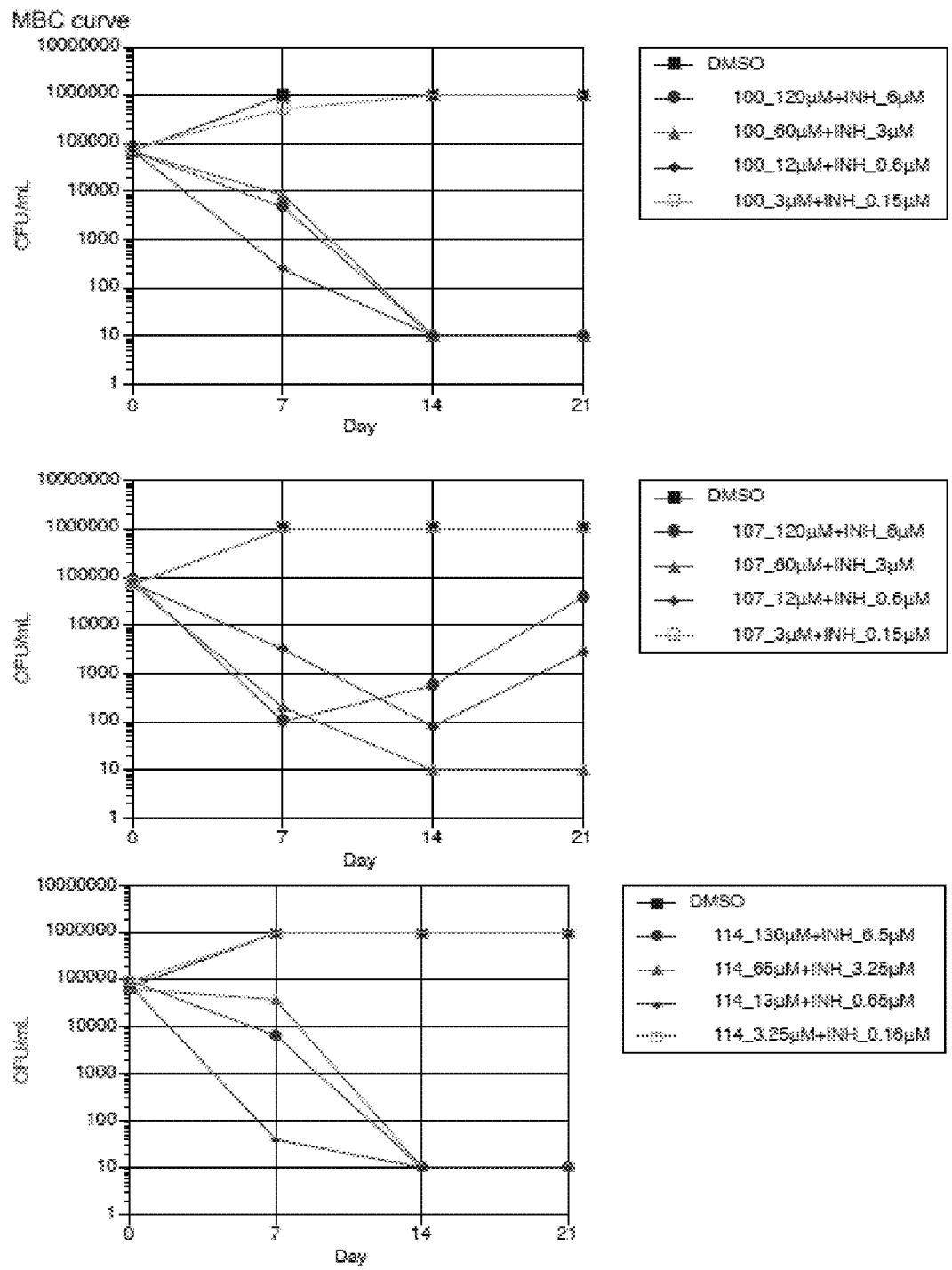
FIG. 1: MBC kill-curve of 100, 107 and 114 with isoniazid (20:1 mixture)

The present invention also provides a compound having the structure:

wherein

α is absent or present and when present is a bond, wherein when $R_3$ and $R_4$ combine to form a cycloalkyl group, then α is absent;

X is —NH—, —NH—NH—, —NH—C(O)—, —NH—C(S)—, —NH—NHC(O)— or —NH—NHC(S)—;

$R_1$ is —H, alkyl, alkenyl, alkynyl, aryl, heteroaryl, C(O)-alkyl, C(O)-haloalkyl, C(O)-cycloalkyl, C(O)-alkenyl, C(O)-alkynyl, C(O)-aryl, C(O)-heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, $SO_2$-alkyl, $SO_2$-haloalkyl, $SO_2$-cycloalkyl, $SO_2$-alkenyl, $SO_2$-alkynyl, $SO_2$-aryl, $SO_2$-heteroaryl or L-(anti-tuberculosis drug);

$R_2$ is H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-N(alkyl)$_2$;

$R_3$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-N(alkyl)$_2$, and $R_4$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, or alkyl-N(alkyl)$_2$, or $R_3$ and $R_4$ combine to form a cycloalkyl group;

$R_5$ is a substituted aryl, substituted heteroaryl, alkylaryl or L-(anti-tuberculosis drug), wherein L is a chemical linker comprising a functional group capable of forming a bond with an anti-tuberculosis drug;

wherein when α is absent, X is NH, and $R_1$, $R_2$, $R_3$ and $R_4$ are each H, then $R_5$ is other than 2-(tert-butyl)-5-(trifluoromethyl)phenyl, 2,5-di-tert-butylphenyl, 4-morpholinophenyl or 2-benzoylphenyl,
or a salt or ester thereof.

The present invention provides a compound having the structure:

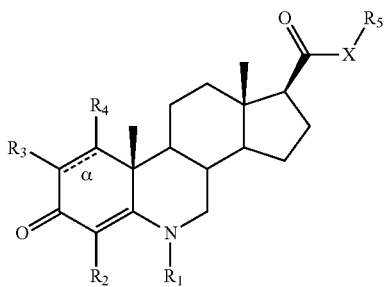

wherein
α is absent or present and when present is a bond,
wherein when $R_3$ and $R_4$ combine to form a cycloalkyl group, then α is absent;
X is —NH—, —NH—NH—, —NH—C(O)—, —NH—C(S)—, —NH—NHC(O)— or —NH—NHC(S)—;
$R_1$ is —H, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, or L-(anti-tuberculosis drug);
$R_2$ is H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-N(alkyl)$_2$;
$R_3$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-N(alkyl)$_2$, and
$R_4$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, or alkyl-N(alkyl)$_2$, or
$R_3$ and $R_4$ combine to form a cycloalkyl group;
$R_5$ is a substituted aryl, substituted heteroaryl, alkylaryl or L-(anti-tuberculosis drug),
wherein L is a chemical linker comprising a functional group capable of forming a bond with an anti-tuberculosis drug;
wherein when α is absent, X is NH, and $R_1$, $R_2$, $R_3$ and $R_4$ are each H, then $R_5$ is other than 2-(tert-butyl)-5-(trifluoromethyl)phenyl, 2,5-di-tert-butylphenyl, 4-morpholinophenyl or 2-benzoylphenyl,
or a salt or ester thereof.

The present invention provides a compound having the structure:

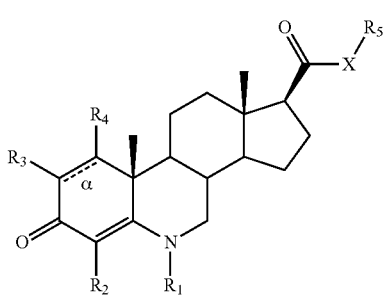

wherein
α is absent or present and when present is a bond,
wherein when $R_3$ and $R_4$ combine to form a cycloalkyl group, then α is absent;
X is —NH—;
$R_1$ is —H, alkyl, alkenyl, alkynyl, aryl, heteroaryl, C(O)-alkyl, C(O)-haloalkyl, C(O)-cycloalkyl, C(O)-alkenyl, C(O)-alkynyl, C(O)-aryl, C(O)-heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, $SO_2$-alkyl, $SO_2$-haloalkyl, $SO_2$-cycloalkyl, $SO_2$-alkenyl, $SO_2$-alkynyl, $SO_2$-aryl, $SO_2$-heteroaryl;
$R_2$ is H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-N(alkyl)$_2$;
$R_3$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-N(alkyl)$_2$, and
$R_4$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, or alkyl-N(alkyl)$_2$, or
$R_3$ and $R_4$ combine to form a cycloalkyl group;
$R_5$ is a substituted aryl or substituted heteroaryl
wherein the substituted aryl is substituted at least at two or more positions with an alkyl or trifluoromethyl;
wherein the substituted heteroaryl is substituted at least at two or more positions with a halogen, methoxy or trifluoromethoxy; and
wherein when α is absent, X is NH, and R_, $R_2$, $R_3$ and $R_4$ are each H, then $R_5$ is other than 2-(tert-butyl)-5-(trifluoromethyl)phenyl or 2,5-di-tert-butylphenyl,
or a salt or ester thereof.

In some embodiments, the compound having the structure:

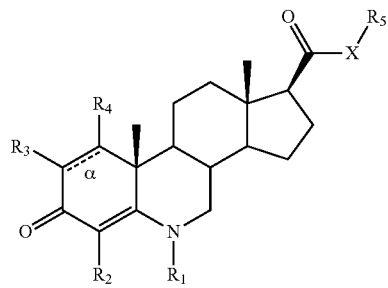

wherein
α is absent or present and when present is a bond,
wherein when $R_3$ and $R_4$ combine to form a cycloalkyl group, then α is absent;
X is —NH—, —NH—NH—, —NH—C(O)—, —NH—C(S)—, —NH—NHC(O)— or —NH—NHC(S)—;
$R_1$ is —H, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, or L-(anti-tuberculosis drug);
$R_2$ is H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-N(alkyl)$_2$;
$R_3$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-N(alkyl)$_2$, and R$_4$ is —H, halo, alkyl, alkenyl, alkynyl, aryl, heteroaryl, CO$_2$-alkyl, CO$_2$-alkenyl, CO$_2$-alkynyl, CO$_2$-aryl, CO$_2$-heteroaryl, cycloalkyl, alkyl-OH, alkyl-NH$_2$, or alkyl-N(alkyl)$_2$, or R$_3$ and R$_4$ combine to form a cycloalkyl group;

R$_5$ is a substituted aryl, substituted heteroaryl, alkylaryl or L-(anti-tuberculosis drug), wherein L is a chemical linker comprising a functional group capable of forming a bond with an anti-tuberculosis drug;

wherein when α is absent, X is NH, and R$_1$, R$_2$, R$_3$ and R$_4$ are each H, then R$_5$ is other than 2-(tert-butyl)-5-(trifluoromethyl)phenyl, 2,5-di-tert-butylphenyl, 3-tert-butylphenyl, 4-morpholinophenyl, 2-benzoylphenyl or 2,5-trifluoromethylphenyl, when α is absent, X is NH, R$_1$ is H or Boc, and R$_2$, R$_3$ and R$_4$ are each H, then R$_5$ is other than 2-trifluoromethoxy-4-halophenyl, 6-(5-fluoro-indol-1-yl)-2-(trifluoromethoxy) pyridin-3-yl or 2-trifluoromethoxy-3-trifluoromethylphenyl, and when α is absent, X is —NH—C(S)—, and R$_1$, R$_2$, R$_3$ and R$_4$ are each H, then R$_5$ is other than 2-ethylpyridin-4-yl, or a salt or ester thereof.

In some embodiments, the compound wherein when α is absent, X is NH, and R$_1$, R$_2$, R$_3$ and R$_4$ are each H, then R$_5$ is other than 2-(tert-butyl)-5-(trifluoromethyl)phenyl, 2,5-di-tert-butylphenyl, 3-tert-butylphenyl, 4-morpholinophenyl, 2-benzoylphenyl or 2,5-trifluoromethylphenyl, and R$_5$ is other than 2-trifluoromethoxy-4-halophenyl, 2-trifluoromethoxy-3-trifluoromethylphenyl, 6-(5-fluoro-indol-1-yl)-2-(trifluoromethoxy) pyridin-3-yl or 2-ethylpyridine.

In some embodiments, the compound wherein when α is absent, X is NH, and R$_1$, R$_2$, R$_3$ and R$_4$ are each H, then R$_5$ is other than 2-(tert-butyl)-5-(trifluoromethyl)phenyl or 2,5-di-tert-butylphenyl, and R$_5$ is other than 2-trifluoromethoxy-4-halophenyl, 2-trifluoromethoxy-3-trifluoromethylphenyl, 2-methylpyridine, 4-morpholinophenyl, 2-benzoylphenyl or 2,5-trifluoromethylphenyl.

In some embodiments, wherein the compound contains at least one t-butyl group.

In some embodiments, wherein the compound contains at least two t-butyl groups.

In some embodiments, the compound wherein when α is absent, X is NH, and R$_1$, R$_2$, R$_3$ and R$_4$ are each H, then R$_5$ is other than 2-trifluoromethoxy-4-halophenyl or 2-trifluoromethoxy-3-trifluoromethylphenyl.

In some embodiments, the compound wherein when α is absent, X is —NH—C(S)—, and R$_1$, R$_2$, R$_3$ and R$_4$ are each H, then R$_5$ is other than 2-ethylpyridin-4-yl.

In some embodiments, the compound wherein when α is absent, X is NH, and R$_1$, R$_2$, R$_3$ and R$_4$ are each H, then R$_5$ is other than 2-(tert-butyl)-5-(trifluoromethyl)phenyl, 2,5-di-tert-butylphenyl, or 2,5-trifluoromethylphenyl.

In some embodiments, the compound wherein when α is absent, X is NH, and R$_1$, R$_2$, R$_3$ and R$_4$ are each H, then R$_5$ is other than 2-(tert-butyl)-5-(trifluoromethyl)phenyl, 2,5-di-tert-butylphenyl or 2,5-trifluoromethylphenyl or 3,5-di-tert-butylphenyl.

In some embodiments, the compound wherein R$_5$ is

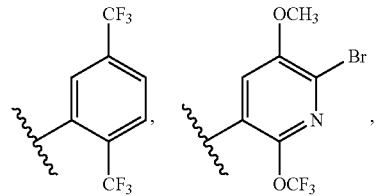

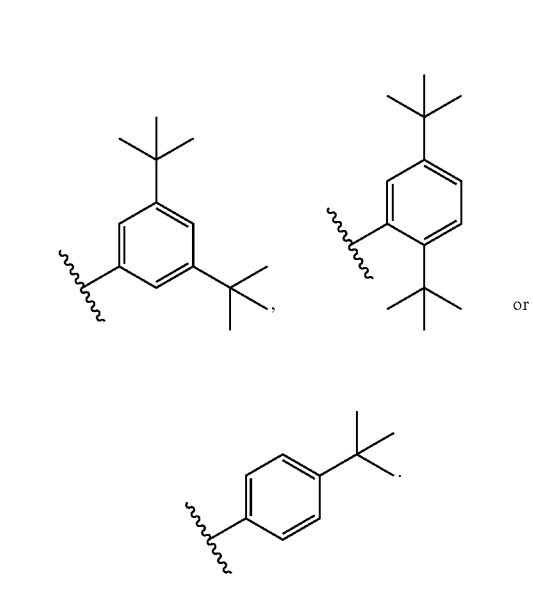

In some embodiments, the compound wherein R$_5$ is

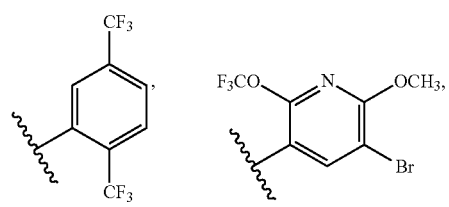

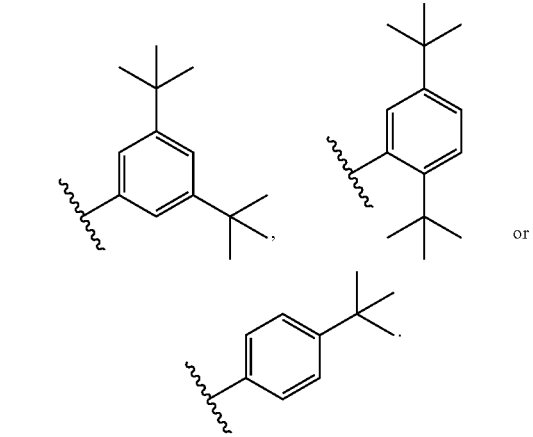

In some embodiments, the compound wherein R₅ is

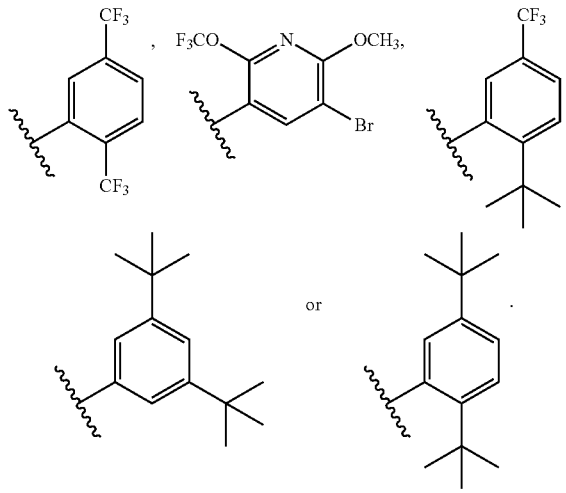

In some embodiments, the compound wherein R₅ is a substituted aryl or substituted heteroaryl.

In some embodiments, the compound wherein R₅ is a substituted aryl.

In some embodiments, the compound wherein R₅ is a substituted heteroaryl.

In some embodiments, the compound wherein the R₅ the substituted aryl or substituted heteroaryl is disubstituted.

In some embodiments, the compound wherein the R₅ the substituted aryl or substituted heteroaryl is trisubstituted.

In some embodiments, the compound wherein the substituted aryl or substituted heteroaryl is substituted with halo, —CN, —CF₃, —OCF₃, -alkyl, -alkenyl, -alkynyl, -aryl, -heteroaryl, —NH₂, —NH-alkyl, —NH-alkenyl, —NH— alkynyl, —NH-aryl, —NH-heteroaryl, —OH, —OAc, —O—C(O)alkyl, —O-alkyl, —O-alkylaryl, —O-alkenyl, —O-alkynyl, —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), —SO₂-(heteroaryl), alkyl-OH, alkyl-O-alkyl, alkyl-NH₂, alkyl-NH-alkyl, alkyl-N(alkyl)₂, cycloalkyl or alkyl-cycloalkyl.

In some embodiments, the compound wherein the substituted aryl or substituted heteroaryl is substituted with halo, —CF₃, —OCF₃, -alkyl or —O-alkyl.

In some embodiments, the compound, wherein the substituted aryl or substituted heteroaryl is substituted with Br, —CF₃, —OCF₃, —CH₃, —C(CH₃)₃ or —OCH₃.

In some embodiments, the compound wherein R₅ has the structure:

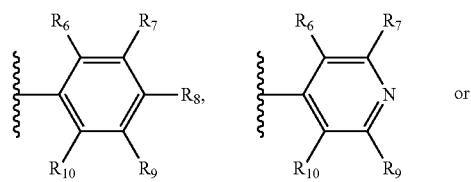

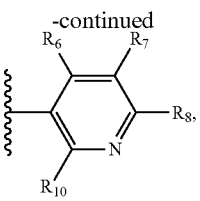

wherein R₆, R₇, R₈, R₉ and R₁₀ are each, independently, —H, halo, —CN, —CF₃, —OCF₃, -alkyl, -alkenyl, -alkynyl, -aryl, -heteroaryl, —NH₂, —NH-alkyl, —NH-alkenyl, —NH-alkynyl, —NH-aryl, —NH-heteroaryl, —OH, —OAc, —O—C(O)alkyl, —O-alkyl, —O-alkylaryl, —O-alkenyl, —O-alkynyl, —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), —SO₂-(heteroaryl), alkyl-OH, alkyl-O-alkyl, alkyl-NH₂, alkyl-NH-alkyl, alkyl-N(alkyl)₂, cycloalkyl or alkyl-cycloalkyl.

In some embodiments, the compound wherein R₅ has the structure:

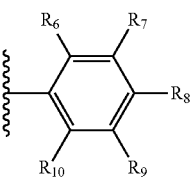

wherein R₆ and R₉ are each, independently, halo, —CN, —CF₃, —OCF₃, -alkyl, -alkenyl, -alkynyl, -aryl, -heteroaryl, —NH₂, —NH-alkyl, —NH-alkenyl, —NH— alkynyl, —NH-aryl, —NH-heteroaryl, —OH, —OAc, —O—C(O)alkyl, —O-alkyl, —O-alkylaryl, —O-alkenyl, —O-alkynyl, —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), —SO₂-(heteroaryl), alkyl-OH, alkyl-O-alkyl, alkyl-NH₂, alkyl-NH-alkyl, alkyl-N(alkyl)₂, cycloalkyl or alkyl-cycloalkyl; and
R₇, R₈ and R₁₀ are each —H.

In some embodiments, the compound wherein R₆ and R₉ are each, independently, halo, —CF₃, —OCF₃, -alkyl or —O-alkyl.

In some embodiments, the compound wherein R; has the structure:

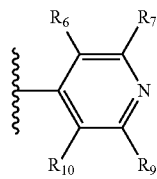

wherein R₇ is halo, —CN, —CF₃, —OCF₃, -alkyl, -alkenyl, -alkynyl, -aryl, -heteroaryl, —NH₂, —NH-alkyl, —NH-alkenyl, —NH-alkynyl, —NH-aryl, —NH— heteroaryl, —OH, —OAc, —O—C(O)alkyl, —O-alkyl, —O-alkylaryl, —O-alkenyl, —O-alkynyl, —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO₂-(alkyl), —SO₂-(aryl), —SO₂-(heteroaryl), alkyl-OH, alkyl-O-alkyl, alkyl-NH$_2$, alkyl-NH-alkyl, alkyl-N(alkyl)$_2$, cycloalkyl or alkyl-cycloalkyl; and R$_6$, R$_9$ and R$_{10}$ are each —H.

In some embodiments, the compound wherein R$_7$ is halo, —CF$_3$, —OCF$_3$, -alkyl or —O-alkyl.

In some embodiments, the compound wherein R$_5$ has the structure:

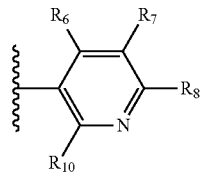

wherein R$_7$, R$_8$ and R$_{10}$ are each, independently, halo, —CN, —CF$_3$, —OCF$_3$, -alkyl, -alkenyl, -alkynyl, -aryl, -heteroaryl, —NH$_2$, —NH-alkyl, —NH— alkenyl, —NH-alkynyl, —NH-aryl, —NH-heteroaryl, —OH, —OAc, —O—C(O)alkyl, —O-alkyl, —O-alkylaryl, —O-alkenyl, —O-alkynyl, —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), —SO$_2$-(heteroaryl), alkyl-OH, alkyl-O-alkyl, alkyl-NH$_2$, alkyl-NH-alkyl, alkyl-N(alkyl)$_2$, cycloalkyl or alkyl-cycloalkyl; and R$_6$ is —H.

In some embodiments, the compound wherein R$_7$, R$_8$ and R$_{10}$ are each, independently, halo, —CF$_3$, —OCF$_3$, -alkyl or —O-alkyl.

In some embodiments, the compound wherein R$_1$ is H, alkyl, or CO$_2$-alkyl.

In some embodiments, the compound wherein R$_1$ is H or —CO$_2$-(t-Bu).

In some embodiments, the compound wherein R$_1$ is H, —CH$_3$ or —CH$_2$CH$_3$.

In some embodiments, the compound wherein R$_2$ is H, alkyl, cycloalkyl or alkyl-N(alkyl)$_2$.

In some embodiments, the compound wherein R$_3$ is H or alkyl.

In some embodiments, the compound wherein R$_4$ is H or alkyl.

In some embodiments, the compound wherein R$_3$ and R$_4$ combine to form a cycloalkyl.

In some embodiments, the compound wherein R$_3$ and R$_4$ combine to form a cyclopropyl.

In some embodiments, the compound wherein R$_1$, R$_2$, R$_3$ and R$_4$ are each —H.

In some embodiments, the compound wherein X is —NH—.

In some embodiments, the compound wherein X is —NH—NH—.

In some embodiments, the compound wherein X is —NH—C(O)— or —NH—C(S)—.

In some embodiments, the compound wherein X is —NH—NHC(O)— or —NH—NHC(S)—.

In some embodiments, the compound wherein
α is absent or present and when present is a bond,
  wherein when R$_3$ and R$_4$ combine to form a cycloalkyl group, then α is absent;
X is —NH—;
R$_1$ is —H, alkyl, or CO$_2$-alkyl;
R$_2$ is H, alkyl, CO$_2$-alkyl or alkyl-N(alkyl)$_2$;
R$_3$ is —H or alkyl, and
R$_4$ is —H or alkyl, or
R$_3$ and R$_4$ combine to form a cycloalkyl group;

R$_5$ is substituted aryl or heteroaryl,
or a salt or ester thereof.

In some embodiments, the compound wherein
α is absent or present and when present is a bond,
  wherein when R$_3$ and R$_4$ combine to form a cycloalkyl group, then α is absent;
X is —NH—;
R$_1$ is —H, alkyl, or CO$_2$-alkyl;
R$_2$ is H, alkyl, CO$_2$-alkyl or alkyl-N(alkyl)$_2$;
R$_3$ is —H or alkyl;
R$_4$ is —H or alkyl; and
R$_5$ is

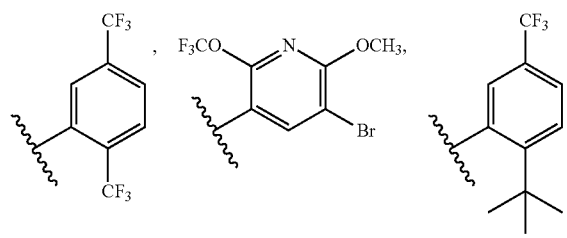

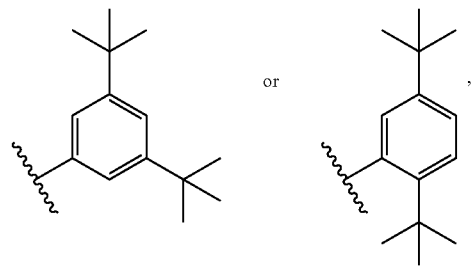

or a salt or ester thereof.

In some embodiments, the compound wherein R$_1$ or R$_5$ is L-(anti-tuberculosis drug).

In some embodiments, the compound wherein the TB drug is isoniazid or ethionamide.

In some embodiments, the compound wherein the anti-tuberculosis drug is pretomanid (PA-824), pyrazinamide, ethambutol, rifabutin, kanamycin, amikacin, capreomycin, streptomycin, levofloxacin, moxifloxacin, ofloxacin, para-aminosalicylic acid, cycloserine, terizidone, thionamide, protionamide, delamanid, bedaquiline or rifampicin.

In some embodiments, the compound wherein L comprises

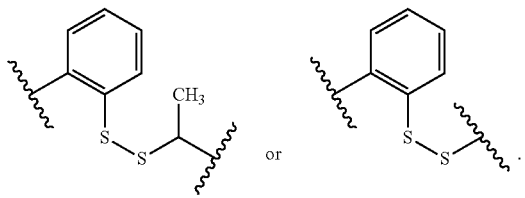 [SMILES: *c1ccccc1SSC(*)C ; *SSc1ccccc1*]

In some embodiments, the compound wherein L has the structure:
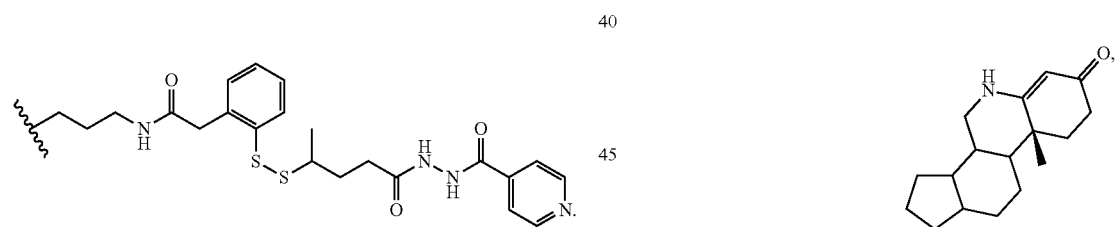
or
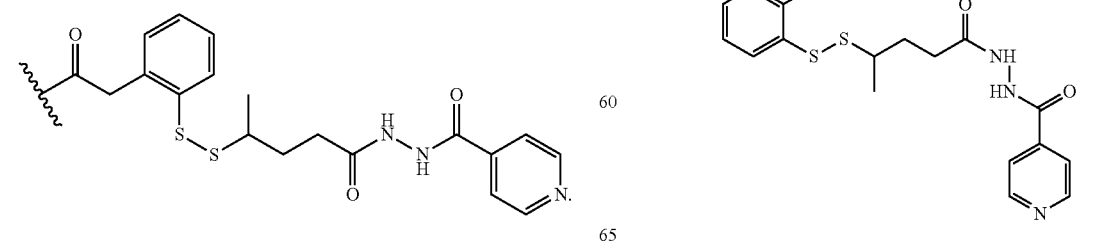
In some embodiments, the compound wherein $R_5$ is
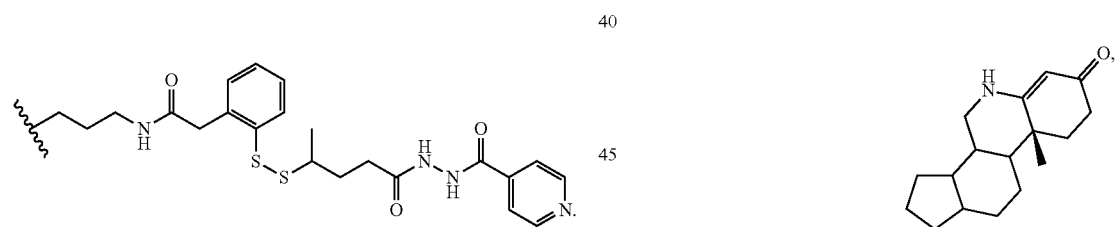
In some embodiments, the compound wherein $R_1$ is
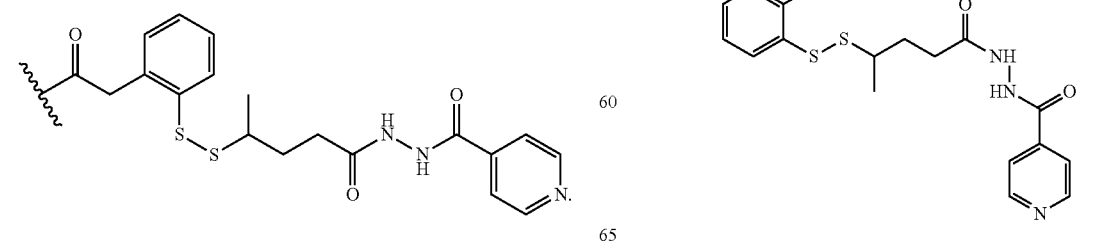
In some embodiments, the compound having the structure:
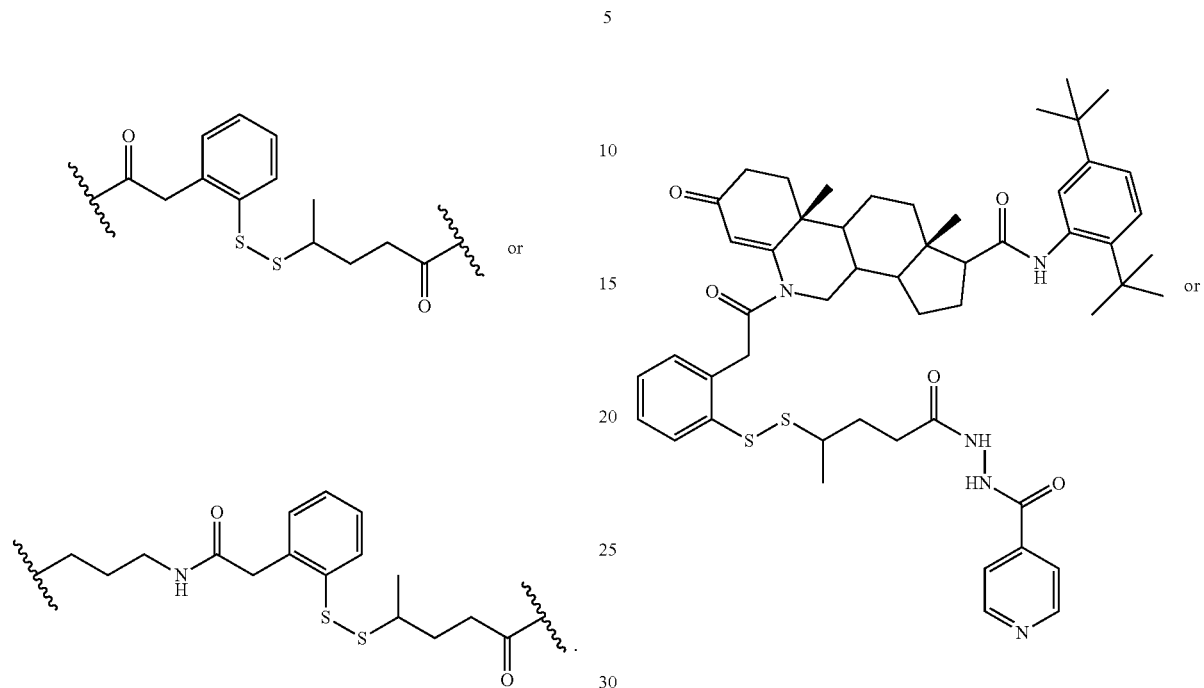
or a salt or ester thereof.

In some embodiments, the compound having the structure:
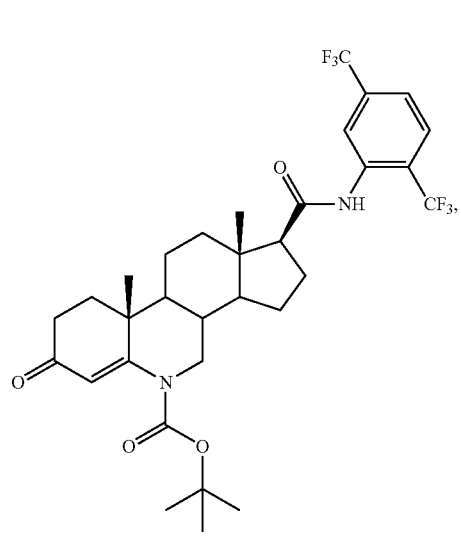
(103)
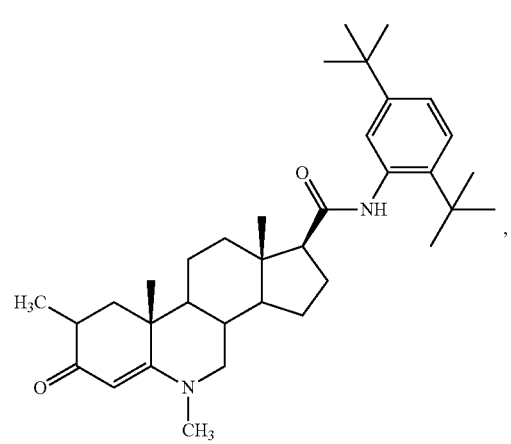
(104)
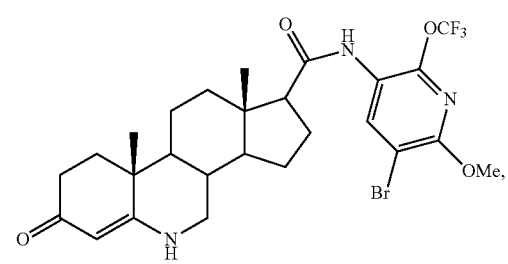
(105)
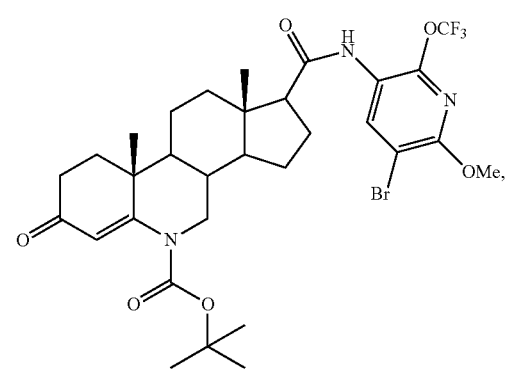
(107)
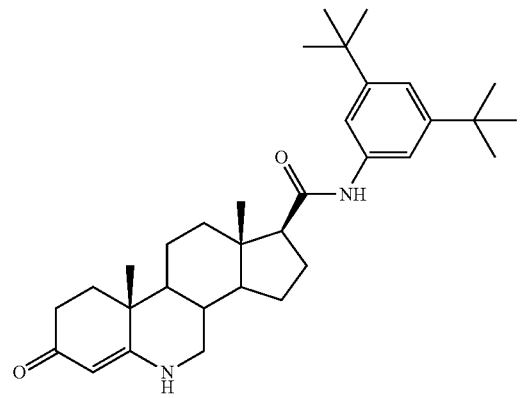
(109)
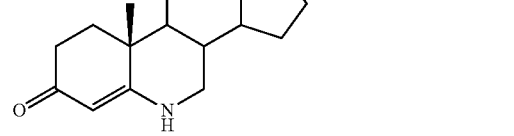
(112)
(113)
or -continued
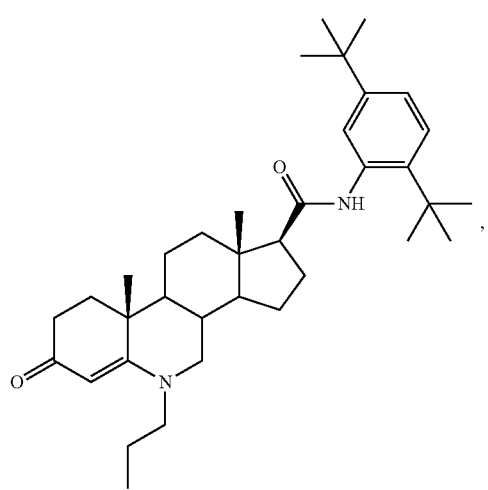
or a salt or ester thereof.
In some embodiments, the compound having the structure:
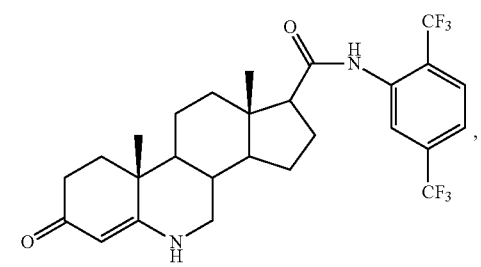
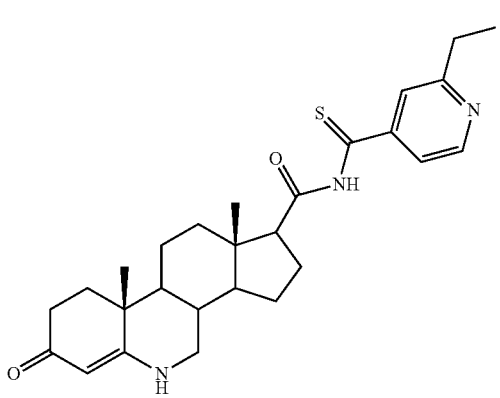
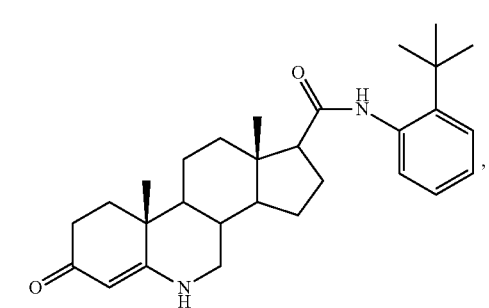
-continued
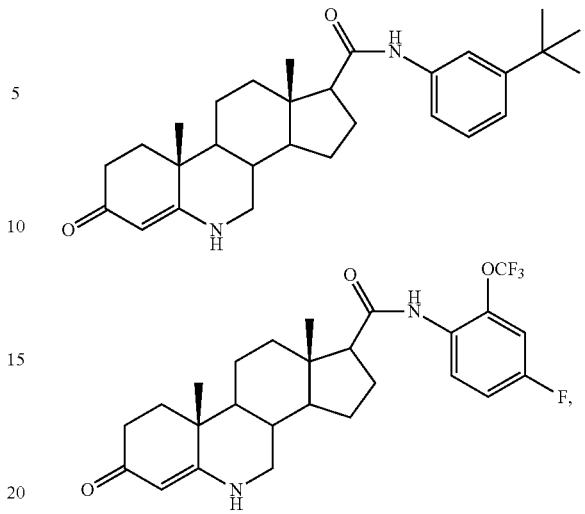
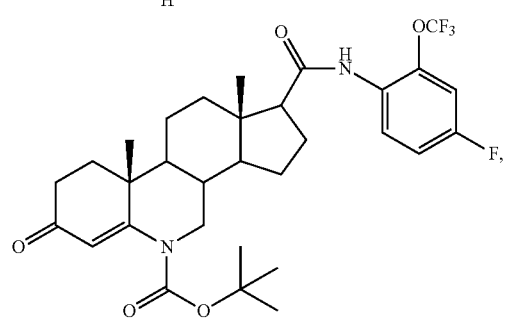
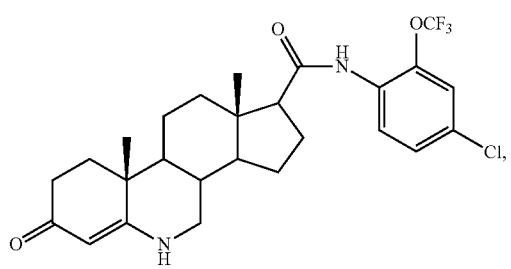
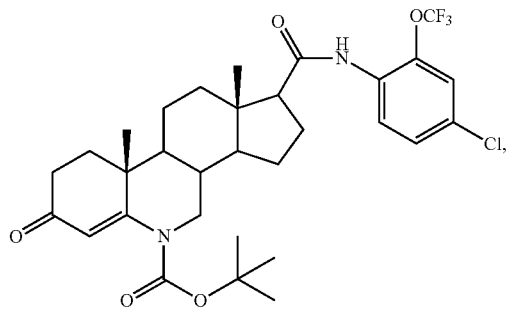
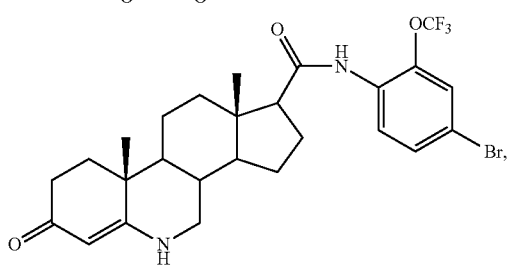

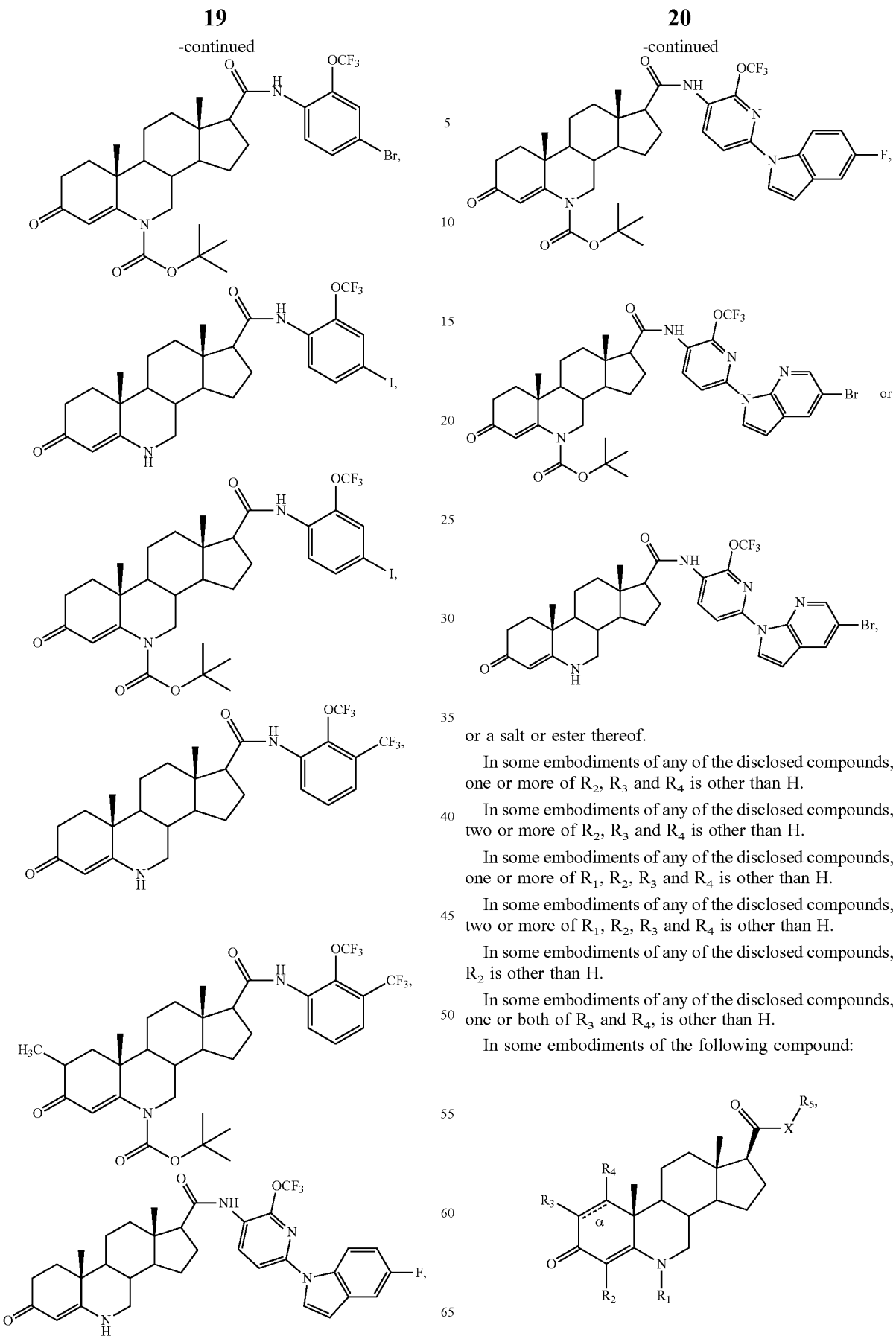

or a salt or ester thereof.

In some embodiments of any of the disclosed compounds, one or more of $R_2$, $R_3$ and $R_4$ is other than H.

In some embodiments of any of the disclosed compounds, two or more of $R_2$, $R_3$ and $R_4$ is other than H.

In some embodiments of any of the disclosed compounds, one or more of $R_1$, $R_2$, $R_3$ and $R_4$ is other than H.

In some embodiments of any of the disclosed compounds, two or more of $R_1$, $R_2$, $R_3$ and $R_4$ is other than H.

In some embodiments of any of the disclosed compounds, $R_2$ is other than H.

In some embodiments of any of the disclosed compounds, one or both of $R_3$ and $R_4$, is other than H.

In some embodiments of the following compound:

$R_5$ is also an unsubstituted aryl or unsubstituted heteroaryl.

In some embodiments, the compound having the structure:

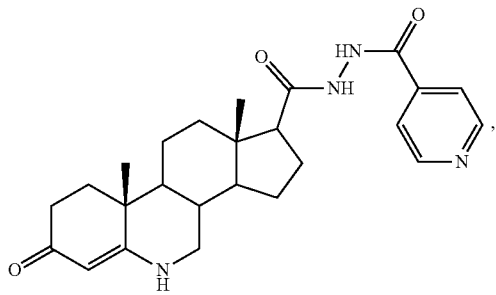 [SMILES: C[C@]12CCC3C(CNC4=CC(=O)CC[C@@]43C)C1CCC2C(=O)NNC(=O)c1ccncc1]

or a salt or ester thereof.

In some embodiments, a pharmaceutical composition comprising the compound of the present invention and a pharmaceutically acceptable carrier.

In some embodiments, a pharmaceutical composition comprising the compound of the present invention, an anti-tuberculosis drug and a pharmaceutically acceptable carrier.

In some embodiments, a pharmaceutical composition comprising the compound of the present invention, isoniazid and a pharmaceutically acceptable carrier.

In some embodiments, a pharmaceutical composition comprising the compound of the present invention, ethionamide and a pharmaceutically acceptable carrier.

In some embodiments, a pharmaceutical composition comprising the compound of the present invention, bedaquiline and a pharmaceutically acceptable carrier.

In some embodiments, a pharmaceutical composition comprising the compound of the present invention, pretomanid and a pharmaceutically acceptable carrier.

In some embodiments, a pharmaceutical composition comprising the compound of the present invention, prothionamide and a pharmaceutically acceptable carrier.

In some embodiments, a method of treating a subject infected with M. tuberculosis comprising administering to the subject an amount of the compound of the present invention so as to thereby treat the subject.

In some embodiments, the M. tuberculosis infection is latent, active, drug-resistant, extensively drug-resistant or multi-drug resistant.

In some embodiments, the infected subject is afflicted with pulmonary tuberculosis or extrapulmonary tuberculosis.

In some embodiments, the method further comprising administering an amount of an anti-tuberculosis drug to the subject.

In some embodiments, the method wherein the amount of anti-tuberculosis drug administered to the subject is at least 25% less than the clinically recommended dose for the subject.

In some embodiments, the method wherein the amount of anti-tuberculosis drug administered to the subject is at least 50% less than the clinically recommended dose for the subject.

In some embodiments, the method wherein the amount of anti-tuberculosis drug administered to the subject is at least 75% less than the clinically recommended dose for the subject.

In some embodiments, the method wherein the amount of the compound and the amount of the anti-tuberculosis drug when taken together is more effective to treat the M. tuberculosis infection than the anti-tuberculosis drug alone.

In some embodiments, the method wherein the amount of the compound causes the M. tuberculosis in the subject to be more susceptible to treatment with the anti-tuberculosis drug.

In some embodiments, the method wherein the amount of the compound enhances the anti-tuberculosis effect of the anti-tuberculosis drug.

In some embodiments, the method, wherein the anti-tuberculosis drug is isoniazid, rifampicin, pyrazinamide, ethambutol or streptomycin or combinations thereof.

In some embodiments, the method wherein the anti-tuberculosis drug is pretomanid (PA-824), pyrazinamide, ethambutol, rifabutin, kanamycin, amikacin, capreomycin, streptomycin, levofloxacin, moxifloxacin, ofloxacin, para-aminosalicylic acid, cycloserine, terizidone, thionamide, protionamide, delamanid or bedaquiline or combinations thereof.

In some embodiments, the method wherein the anti-tuberculosis drug is isoniazid or ethionamide.

In some embodiments, the method wherein the anti-tuberculosis drug is isoniazid, ethionamide, bedaquiline or pretomanid.

In some embodiments, the method wherein the anti-tuberculosis drug is isoniazid, ethionamide, bedaquiline or protionamide.

In some embodiments, the method wherein the mole ratio of compound and the isoniazid or ethionamide administered to the subject is 1000:1, 100:1, 10:1, 2:1, 1:1, 1:2, 1:10, 1:100 or 1:1000.

In some embodiments, the method wherein the subject is also infected with human immunodeficiency virus (HIV).

The present invention also provides a method of treating a subject infected with M. tuberculosis comprising administering to the subject an amount of the compound having the structure:

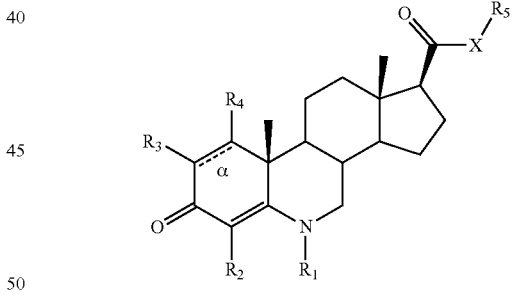

wherein

α is absent or present and when present is a bond,
  wherein when $R_3$ and $R_4$ combine to form a cycloalkyl group, then α is absent;

X is —NH—, —NH—NH—, —NH—C(O)—, —NH—C(S)—, —NH—NHC(O)— or —NH—NHC(S)—;

$R_1$ is —H, alkyl, alkenyl, alkynyl, aryl, heteroaryl, C(O)-alkyl, C(O)-haloalkyl, C(O)-cycloalkyl, C(O)-alkenyl, C(O)-alkynyl, C(O)-aryl, C(O)-heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, $SO_2$-alkyl, $SO_2$-haloalkyl, $SO_2$-cycloalkyl, $SO_2$-alkenyl, $SO_2$-alkynyl, $SO_2$-aryl, $SO_2$-heteroaryl or L-(anti-tuberculosis drug);

$R_2$ is H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-$N(alkyl)_2$;

$R_3$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-$N(alkyl)_2$, and $R_4$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, or alkyl-$N(alkyl)_2$, or $R_3$ and $R_4$ combine to form a cycloalkyl group;

$R_5$ is substituted aryl, substituted heteroaryl or alkylaryl, wherein when α is absent, X is NH, and $R_1$, $R_2$, $R_3$ and $R_4$ are each H, then $R_5$ is other than 3-tert-butylphenyl, 4-morpholinophenyl, 2-benzoylphenyl or 2,5-trifluoromethylphenyl, when α is absent, X is NH, $R_R$ is H or Boc, and $R_2$, $R_3$ and $R_4$ are each H, then $R_5$ is other than 2-trifluoromethoxy-4-halophenyl, 6-(5-fluoro-indol-1-yl)-2-(trifluoromethoxy) pyridin-3-yl or 2-trifluoromethoxy-3-trifluoromethylphenyl, and when α is absent, X is —NH—C(S)—, and $R_1$, $R_2$, $R_3$ and $R_4$ are each H, then $R_5$ is other than 2-ethylpyridin-4-yl, or a salt or ester thereof, in combination with an anti-tuberculosis drug, so as to thereby treat the subject.

The present invention also provides a method of treating a subject infected with *M. tuberculosis* comprising administering to the subject an amount of the compound having the structure:

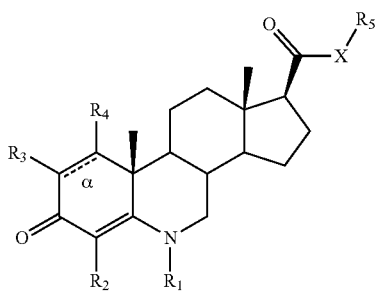

wherein

α is absent or present and when present is a bond,
  wherein when $R_3$ and $R_4$ combine to form a cycloalkyl group, then α is absent;

X is —NH—, —NH—NH—, —NH—C(O)—, —NH—C(S)—, —NH—NHC(O)— or —NH—NHC(S)—;

$R_1$ is —H, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH or alkyl-$NH_2$;

$R_2$ is H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-$N(alkyl)_2$;

$R_3$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-$N(alkyl)_2$, and $R_4$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, or alkyl-$N(alkyl)_2$, or $R_3$ and $R_4$ combine to form a cycloalkyl group;

$R_5$ is substituted aryl, substituted heteroaryl or alkylaryl, wherein when α is absent, X is NH, and $R_1$, $R_2$, $R_3$ and $R_4$ are each H, then $R_5$ is other than 3-tert-butylphenyl, 4-morpholinophenyl, 2-benzoylphenyl or 2,5-trifluoromethylphenyl, when α is absent, X is NH, $R_1$ is H or Boc, and $R_2$, $R_3$ and $R_4$ are each H, then $R_5$ is other than 2-trifluoromethoxy-4-halophenyl, 6-(5-fluoro-indol-1-yl)-2-(trifluoromethoxy) pyridin-3-yl or 2-trifluoromethoxy-3-trifluoromethylphenyl, and when α is absent, X is —NH—C(S)—, and $R_1$, $R_2$, $R_3$ and $R_4$ are each H, then $R_5$ is other than 2-ethylpyridin-4-yl, or a salt or ester thereof, in combination with an anti-tuberculosis drug, so as to thereby treat the subject.

In some embodiments of the above method, the compound wherein

α is absent or present and when present is a bond,
  wherein when $R_3$ and $R_4$ combine to form a cycloalkyl group, then α is absent;

X is —NH—;

$R_1$ is —H, alkyl, alkenyl, alkynyl, aryl, heteroaryl, C(O)-alkyl, C(O)-haloalkyl, C(O)-cycloalkyl, C(O)-alkenyl, C(O)-alkynyl, C(O)-aryl, C(O)-heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, $SO_2$-alkyl, $SO_2$-haloalkyl, $SO_2$-cycloalkyl, $SO_2$-alkenyl, $SO_2$-alkynyl, $SO_2$-aryl, $SO_2$-heteroaryl;

$R_2$ is H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-$N(alkyl)_2$;

$R_3$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$ or alkyl-$N(alkyl)_2$, and $R_4$ is —H, halo, alkyl, alkenyl, alkynyl, aryl, heteroaryl, $CO_2$-alkyl, $CO_2$-alkenyl, $CO_2$-alkynyl, $CO_2$-aryl, $CO_2$-heteroaryl, cycloalkyl, alkyl-OH, alkyl-$NH_2$, or alkyl-$N(alkyl)_2$, or $R_3$ and $R_4$ combine to form a cycloalkyl group;

$R_5$ is a substituted aryl or substituted heteroaryl
wherein the substituted aryl is substituted at least at two or more positions with an alkyl or trifluoromethyl;
wherein the substituted heteroaryl is substituted at least at two or more positions with a halogen, methoxy or trifluoromethoxy; and or a salt or ester thereof.

In some embodiments of the method, the compound wherein when α is absent, X is NH, and $R_1$, $R_2$, $R_3$ and $R_4$ are each H, then $R_5$ is other than 2-(tert-butyl)-5-(trifluoromethyl)phenyl, 2,5-di-tert-butylphenyl, 3-tert-butylphenyl, 4-morpholinophenyl, 2-benzoylphenyl or 2,5-trifluoromethylphenyl, and $R_5$ is other than 2-trifluoromethoxy-4-halophenyl, 2-trifluoromethoxy-3-trifluoromethylphenyl, 6-(5-fluoro-indol-1-yl)-2-(trifluoromethoxy) pyridin-3-yl or 2-ethylpyridine.

In some embodiments of the method, the compound wherein when α is absent, X is NH, and $R_1$, $R_2$, $R_3$ and $R_4$ are each H, then $R_5$ is other than 2-(tert-butyl)-5-(trifluoromethyl)phenyl or 2,5-di-tert-butylphenyl, and $R_5$ is other than 2-trifluoromethoxy-4-halophenyl, 2-trifluoromethoxy-3-trifluoromethylphenyl, 2-methylpyridine, 4-morpholinophenyl, 2-benzoylphenyl or 2,5-trifluoromethylphenyl.

In some embodiments of the method, wherein the compound contains at least one t-butyl group.

In some embodiments of the method, wherein the compound contains at least two t-butyl groups.

In some embodiments of the method, the compound wherein when α is absent, X is NH, and $R_1$, $R_2$, $R_3$ and $R_4$ are each H, then $R_5$ is other than 2-trifluoromethoxy-4-halophenyl or 2-trifluoromethoxy-3-trifluoromethylphenyl.

In some embodiments of the method, the compound wherein when α is absent, X is —NH—C(S)—, and $R_1$, $R_2$, $R_3$ and $R_4$ are each H, then $R_5$ is other than 2-ethylpyridin-4-yl, In some embodiments, the method wherein $R_5$ is

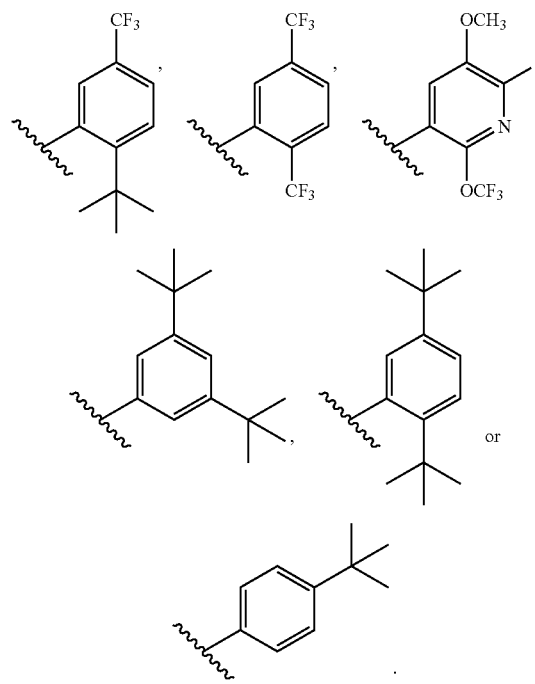

In some embodiments, the method wherein $R_5$ is

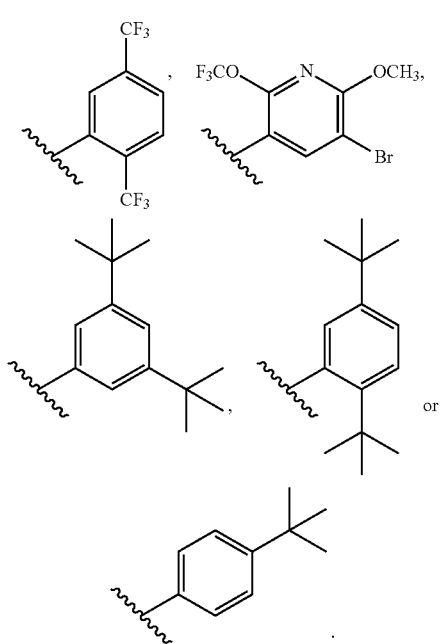

In some embodiments, the method wherein $R_5$ is

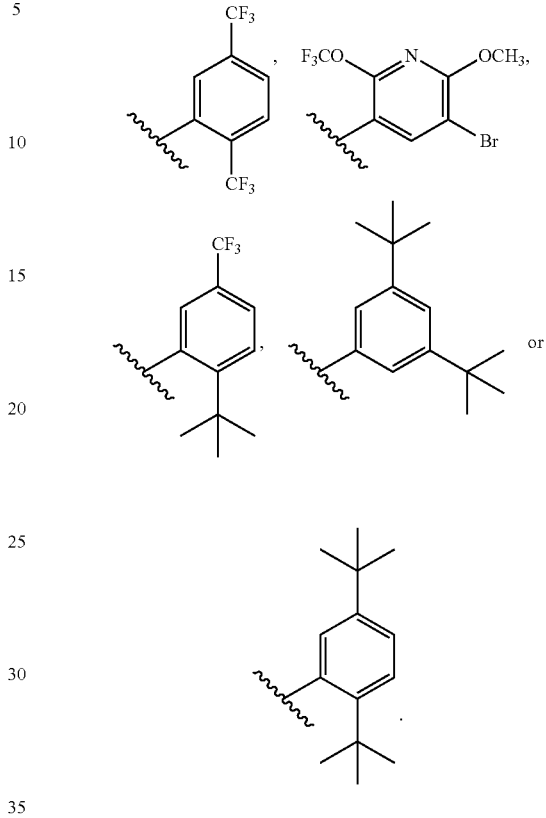

In some embodiments, the method wherein $R_5$ is a substituted aryl or substituted heteroaryl.

In some embodiments, the method wherein $R_2$ is a substituted aryl.

In some embodiments, the method wherein $R_5$ is a substituted heteroaryl.

In some embodiments, the method wherein the $R_5$ the substituted aryl or substituted heteroaryl is disubstituted.

In some embodiments, the method wherein the $R_5$ the substituted aryl or substituted heteroaryl is trisubstituted.

In some embodiments, the method wherein the substituted aryl or substituted heteroaryl is substituted with halo, —CN, —CF$_3$, —OCF$_3$, -alkyl, -alkenyl, -alkynyl, -aryl, -heteroaryl, —NH$_2$, —NH-alkyl, —NH-alkenyl, —NH-alkynyl, —NH-aryl, —NH-heteroaryl, —OH, —OAc, —O—C(O)alkyl, —O-alkyl, —O-alkylaryl, —O-alkenyl, —O-alkynyl, —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), —SO$_2$-(heteroaryl), alkyl-OH, alkyl-O-alkyl, alkyl-NH$_2$, alkyl-NH-alkyl, alkyl-N(alkyl)$_2$, cycloalkyl or alkyl-cycloalkyl.

In some embodiments, the method wherein the substituted aryl or substituted heteroaryl is substituted with halo, —CF$_3$, —OCF$_3$, -alkyl or —O-alkyl.

In some embodiments, the method wherein the substituted aryl or substituted heteroaryl is substituted with Br, —CF$_3$, —OCF$_3$, —CH$_3$, —C(CH$_3$)$_3$ or —OCH$_3$.

In some embodiments, the method wherein $R_5$ has the structure:

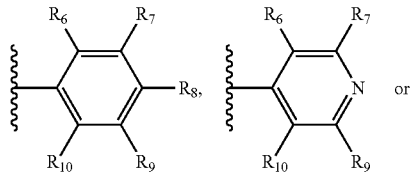

or

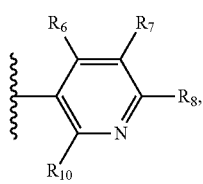

wherein $R_6$, $R_7$, $R_8$, $R_9$ and $R_{10}$ are each, independently, —H, halo, —CN, —CF$_3$, —OCF$_2$, -alkyl, -alkenyl, -alkynyl, -aryl, -heteroaryl, —NH$_2$, —NH-alkyl, —NH-alkenyl, —NH-alkynyl, —NH-aryl, —NH-heteroaryl, —OH, —OAc, —O—C(O)alkyl, —O-alkyl, —O-alkylaryl, —O-alkenyl, —O-alkynyl, —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), —SO$_2$-(heteroaryl), alkyl-OH, alkyl-O-alkyl, alkyl-NH$_2$, alkyl-NH-alkyl, alkyl-N(alkyl)$_2$, cycloalkyl or alkyl-cycloalkyl.

In some embodiments, the method wherein $R_5$ has the structure:

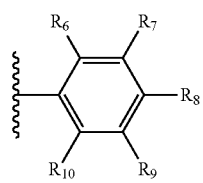

wherein $R_6$ and $R_9$ are each, independently, halo, —CN, —CF$_3$, —OCF$_3$, -alkyl, -alkenyl, -alkynyl, -aryl, -heteroaryl, —NH$_2$, —NH-alkyl, —NH-alkenyl, —NH— alkynyl, —NH-aryl, —NH-heteroaryl, —OH, —OAc, —O—C(O)alkyl, —O-alkyl, —O-alkylaryl, —O-alkenyl, —O-alkynyl, —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), —SO$_2$-(heteroaryl), alkyl-OH, alkyl-O-alkyl, alkyl-NH$_2$, alkyl-NH-alkyl, alkyl-N(alkyl)$_2$, cycloalkyl or alkyl-cycloalkyl; and $R_7$, $R_8$ and $R_{10}$ are each —H.

In some embodiments, the method wherein $R_6$ and $R_9$ are each, independently, halo, —CF$_3$, —OCF$_3$, -alkyl or —O-alkyl.

In some embodiments, the method wherein $R_5$ has the structure:

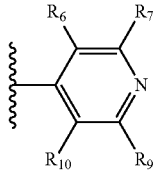

wherein $R_7$ is halo, —CN, —CF$_3$, —OCF$_3$, -alkyl, -alkenyl, -alkynyl, -aryl, -heteroaryl, —NH$_2$, —NH-alkyl, —NH-alkenyl, —NH-alkynyl, —NH-aryl, —NH-heteroaryl, —OH, —OAc, —O—C(O)alkyl, —O-alkyl, —O-alkylaryl, —O-alkenyl, —O-alkynyl, —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), —SO$_2$-(heteroaryl), alkyl-OH, alkyl-O-alkyl, alkyl-NH$_2$, alkyl-NH-alkyl, alkyl-N(alkyl)$_2$, cycloalkyl or alkyl-cycloalkyl; and $R_6$, $R_9$ and $R_{10}$ are each —H.

In some embodiments, the method wherein $R_7$ is halo, —CF$_3$, —OCF$_3$, -alkyl or —O-alkyl.

In some embodiments, the method wherein $R_5$ has the structure:

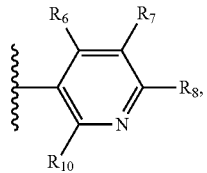

wherein $R_7$, $R_8$ and $R_{10}$ are each, independently, halo, —CN, —CF$_3$, —OCF$_3$, -alkyl, -alkenyl, -alkynyl, -aryl, -heteroaryl, —NH$_2$, —NH-alkyl, —NH— alkenyl, —NH-alkynyl, —NH-aryl, —NH-heteroaryl, —OH, —OAc, —O—C(O)alkyl, —O-alkyl, —O-alkylaryl, —O-alkenyl, —O-alkynyl, —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), —SO$_2$-(heteroaryl), alkyl-OH, alkyl-O-alkyl, alkyl-NH$_2$, alkyl-NH-alkyl, alkyl-N(alkyl)$_2$, cycloalkyl or alkyl-cycloalkyl; and $R_6$ is —H.

In some embodiments, the method wherein $R_7$, $R_8$ and $R_{10}$ are each, independently, halo, —CF$_3$, —OCF$_3$, -alkyl or —O-alkyl.

In some embodiments, the method wherein $R_1$ is H, alkyl, or CO$_2$-alkyl.

In some embodiments, the method wherein $R_1$ is H, —CH$_3$, —CH$_2$CH$_3$ or CO$_2$(t-Bu)

In some embodiments, the method wherein $R_1$ is H.

In some embodiments, the method wherein $R_2$ is H, alkyl, cycloalkyl or alkyl-N(alkyl)$_2$.

In some embodiments, the method wherein $R_3$ is H or alkyl.

In some embodiments, the method wherein $R_4$ is H or alkyl.

In some embodiments, the method wherein $R_3$ and $R_4$ combine to form a cycloalkyl.

In some embodiments, the method wherein $R_3$ and $R_4$ combine to form a cyclopropyl.

In some embodiments, the method wherein $R_1$, $R_2$, $R_3$ and $R_4$ are each —H.

In some embodiments, the method wherein X is —NH—.

In some embodiments, the method wherein X is —NH—NH—.

In some embodiments, the method wherein X is —NH—C(O)— or —NH—C(S)—.

In some embodiments, the method wherein X is —NH—NHC(O)— or —NH—NHC(S)—.

In some embodiments, the method wherein
α is absent or present and when present is a bond,
  wherein when $R_3$ and $R_4$ combine to form a cycloalkyl group, then α is absent;
X is —NH—;
$R_1$ is —H, alkyl, or $CO_2$-alkyl; $R_2$ is H, alkyl, $CO_2$-alkyl or alkyl-N(alkyl)$_2$;
$R_3$ is —H or alkyl, and
$R_4$ is —H or alkyl, or
$R_3$ and $R_4$ combine to form a cycloalkyl group;
$R_5$ is a substituted aryl or heteroaryl,
or a salt or ester thereof.

In some embodiments, the method wherein
α is absent or present and when present is a bond,
  wherein when $R_3$ and $R_4$ combine to form a cycloalkyl group, then α is absent;
X is —NH—;
$R_1$ is —H, alkyl, or $CO_2$-alkyl;
$R_2$ is H, alkyl, $CO_2$-alkyl or alkyl-N(alkyl)$_2$;
$R_3$ is —H or alkyl, and
$R_4$ is —H or alkyl, or
$R_3$ and $R_4$ combine to form a cycloalkyl group;
$R_5$ is

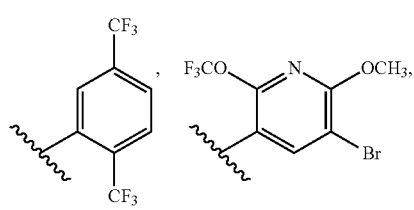

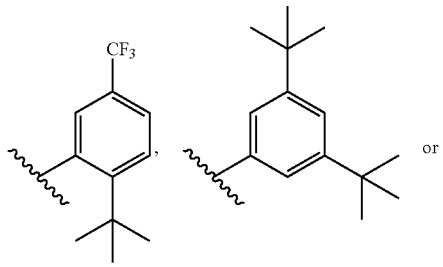

or

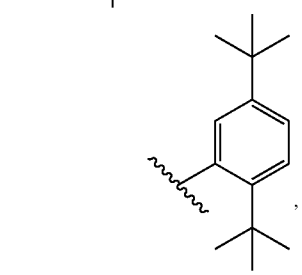

, or a salt or ester thereof.

In some embodiments, the method wherein the compound has the structure:

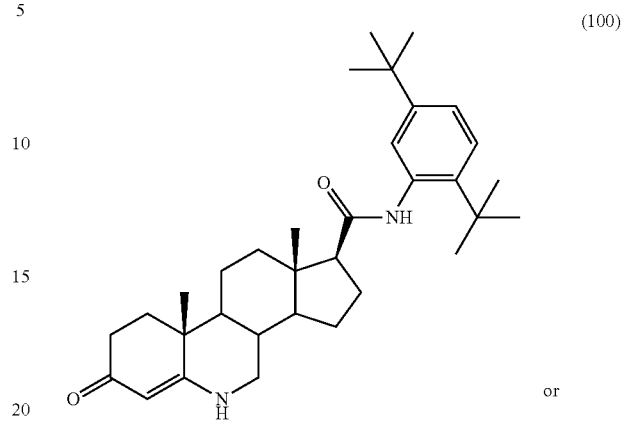

(100)

or

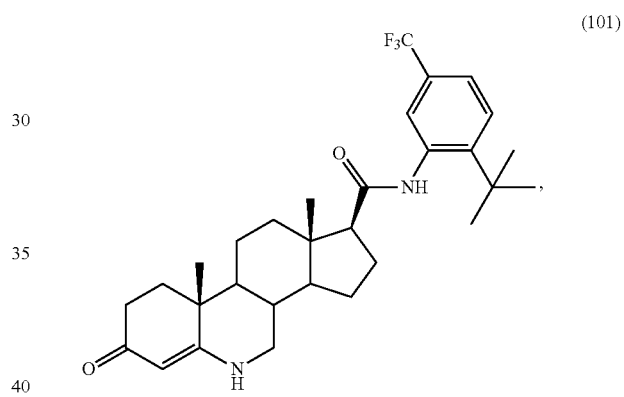

(101)

, or a salt or ester thereof.

In some embodiments, the method wherein the compound has the structure:

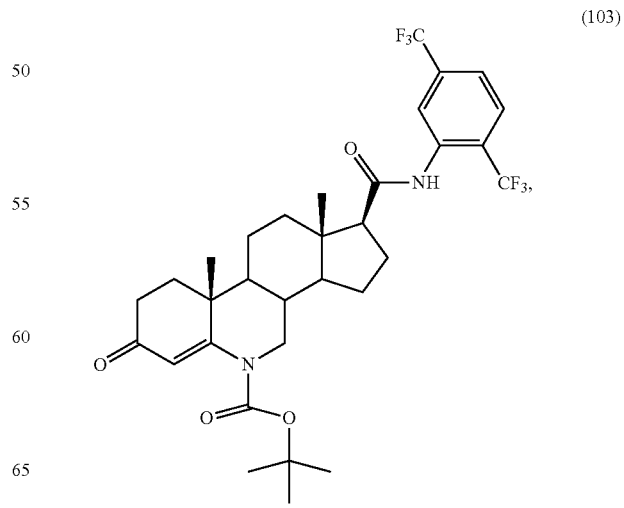

(103)

-continued

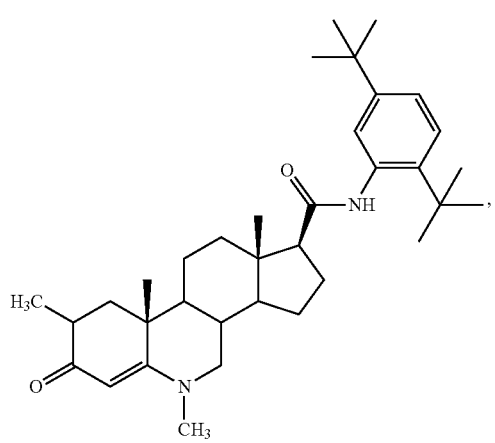
(104)

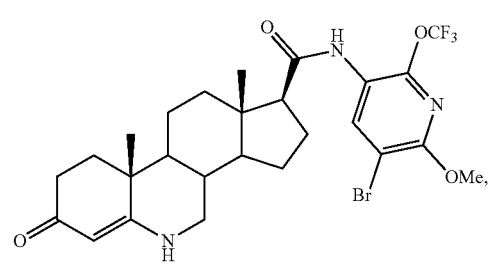
(105)

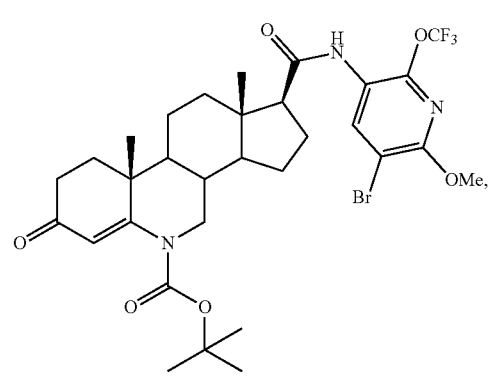
(107)

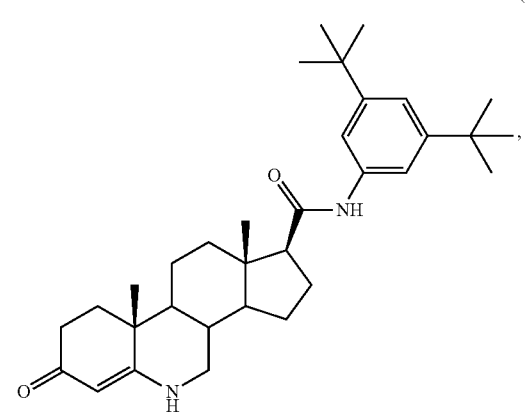
(109)

-continued

(112)

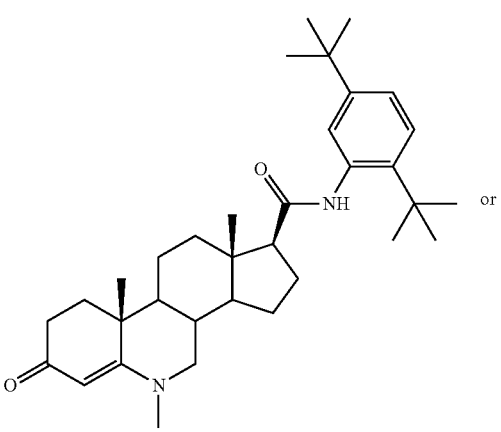
(113)

or

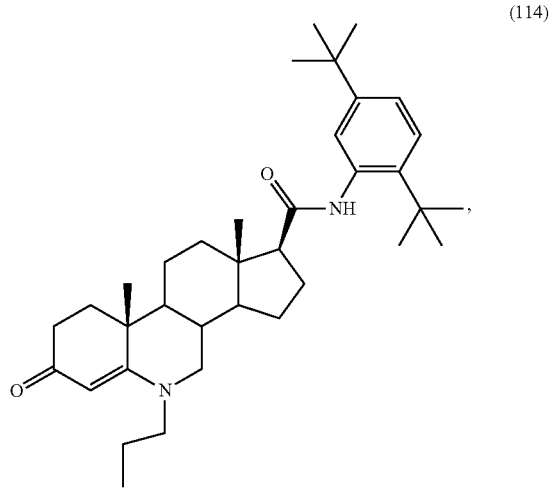
(114)

or a salt or ester thereof.

In some embodiments, the method wherein the *M. tuberculosis* infection is latent, active, drug-resistant, extensively drug-resistant or multi-drug resistant.

In some embodiments, the method wherein the infected subject is afflicted with pulmonary tuberculosis or extrapulmonary tuberculosis.

In some embodiments, the method wherein the amount of anti-tuberculosis drug administered to the subject is 25% less than the clinically recommended dose for the subject.

In some embodiments, the method wherein the amount of anti-tuberculosis drug administered to the subject is 50% less than the clinically recommended dose for the subject.

In some embodiments, the method wherein the amount of anti-tuberculosis drug administered to the subject is 75% less than the clinically recommended dose for the subject.

In some embodiments, the method wherein the amount of the compound and the amount of the anti-tuberculosis drug when taken together is more effective to treat the *M. tuberculosis* infection than the anti-tuberculosis drug alone.

In some embodiments, the method wherein the amount of the compound causes the *M. tuberculosis* in the subject to be more susceptible to treatment with the anti-tuberculosis drug.

In some embodiments, the method wherein the amount of the compound enhances the anti-tuberculosis effect of the anti-tuberculosis drug.

In some embodiments, the method wherein the anti-tuberculosis drug is isoniazid, rifampicin, pyrazinamide, ethambutol or streptomycin or combinations thereof.

In some embodiments, the method wherein the anti-tuberculosis drug is pretomanid (PA-824), pyrazinamide, ethambutol, rifabutin, kanamycin, amikacin, capreomycin, streptomycin, levofloxacin, moxifloxacin, ofloxacin, para-aminosalicylic acid, cycloserine, terizidone, thionamide, protionamide, delamanid or bedaquiline or combinations thereof.

In some embodiments, the method wherein the anti-tuberculosis drug is isoniazid or ethionamide.

In some embodiments, the method wherein the anti-tuberculosis drug is isoniazid, ethionamide, bedaquiline or pretomanid.

In some embodiments, the method wherein the anti-tuberculosis drug is isoniazid, ethionamide, bedaquiline or protionamide.

In some embodiments, the method wherein the mole ratio of compound and the isoniazid or ethionamide administered to the subject is 1000:1, 100:1, 10:1, 2:1, 1:1, 1:2, 1:10, 1:100 or 1:1000.

In some embodiments, the method wherein the subject is also infected with human immunodeficiency virus (HIV).

In some embodiments, the compound having the structure

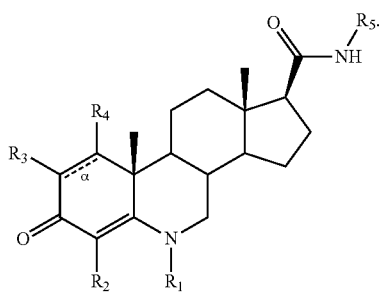

In some embodiments, the compound having the structure

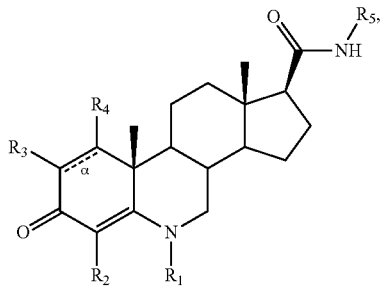

wherein $R_1$ is $CO_2$-alkyl.

In some embodiments, the compound having the structure

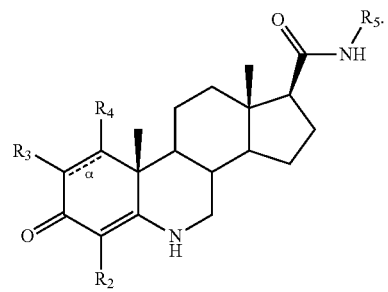

In some embodiments, the compound having the structure

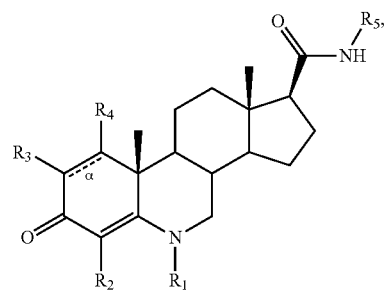

wherein $R_1$ is alkyl.

In some embodiments of any of the disclosed methods, the compound having the structure

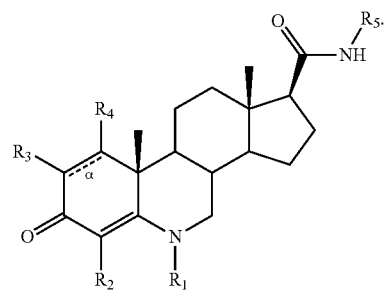

In some embodiments of any of the disclosed methods, the compound having the structure

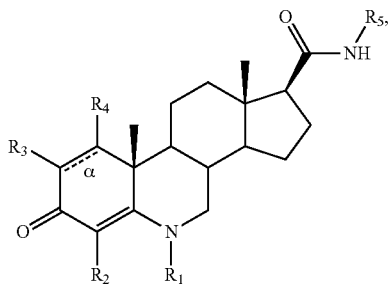

wherein $R_1$ is $CO_2$-alkyl.

In some embodiments of any of the disclosed methods, the compound having the structure

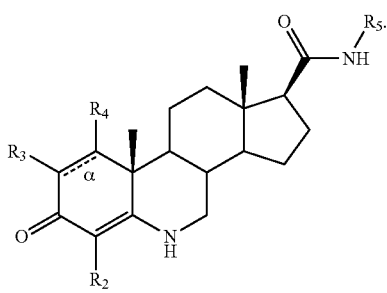

In some embodiments of any of the disclosed methods, the compound having the structure

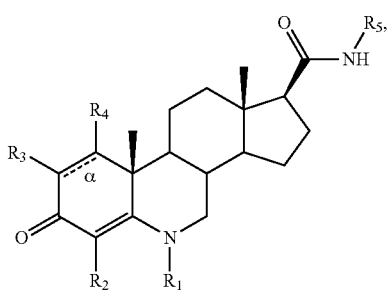

wherein $R_1$ is alkyl.

In some embodiments, the compound wherein X is —NH—; and $R_1$ is $CO_2$-alkyl, $CO_2$-alkenyl, $CO_2$-alkynyl, $CO_2$-aryl or $CO_2$-heteroaryl.

In some embodiments, the compound wherein X is —NH—; and $R_1$ is $CO_2$-alkyl.

In some embodiments, the compound of the present invention having a cLogP greater than or equal to about 4. Compounds having a cLogP greater than or equal to about 4 include, but are not limited to, compounds 105 and 112.

In some embodiments, the compound of the present invention having a cLogP greater than or equal to about 5. Compounds having a cLogP greater than or equal to about 5 include, but are not limited to, compounds 100, 101, 103, 104, 107, 109, 113 and 114.

In some embodiments, the compound of the present invention having a critical volume greater than or equal to about 1400 $cm^3$/mol. Examples of compounds having a critical volume greater than or equal to about 1400 $cm^3$/mol include, but are not limited to, compounds 100, 101, 105 and 109.

In some embodiments, the compound of the present invention having a critical volume greater than or equal to about 1600 $cm^3$/mol. Examples of compounds having a critical volume greater than or equal to about 1600 $cm^3$/mol include, but are not limited to, compounds 103, 104, 107, 113 and 104.

In some embodiments, the compound of the present invention having a topological polar surface area less than 60 $Å^2$.

In some embodiments, the compound of the present invention having a topological polar surface area less than 50 $Å^2$.

The present invention also provides a method of treating a subject infected with M. tuberculosis comprising administering to the subject an amount of the compound of the present invention in combination with one or more anti-tuberculosis drugs so as to thereby treat the subject.

The present invention also provides a method of treating a subject infected with M. tuberculosis comprising administering to the subject an amount of the compound of the present invention in combination with two or more anti-tuberculosis drugs so as to thereby treat the subject.

The present invention also provides a method of treating a subject infected with M. tuberculosis comprising administering to the subject an amount of the compound of the present invention in combination with three or more anti-tuberculosis drugs so as to thereby treat the subject.

The present invention also provides a method of treating a subject infected with M. tuberculosis comprising administering to the subject an amount of the compound of the present invention in combination with four or more anti-tuberculosis drugs so as to thereby treat the subject.

The compounds of the present invention enhance the effectiveness of anti-tuberculosis agents such as isoniazid, thereby providing shorter, more effective, less toxic and/or less expensive TB regimes.

In some embodiments, the method wherein the amount of the compound reduces the duration of treatment with the anti-tuberculosis agent by 10% or more.

In some embodiments, the method wherein the amount of the compound reduces the duration of treatment with the anti-tuberculosis agent by 20% or more.

In some embodiments, the method wherein the amount of the compound reduces the duration of treatment with the anti-tuberculosis agent by 50% or more.

In some embodiments, the method wherein the amount of the compound reduces the duration of treatment with the anti-tuberculosis agent by 75% or more.

In some embodiments, the method wherein the amount of the compound reduces the duration of treatment with the anti-tuberculosis agent by 90%.

In some embodiments, the method wherein the amount of the compound enhances the effectiveness of the amount of the anti-tuberculosis agent administered to the subject.

In some embodiments, the method wherein the amount of the compound reduces the amount of anti-tuberculosis agent needed to effectively treat the tuberculosis.

In some embodiments, the method wherein the amount of the compound and the amount of the anti-tuberculosis agent when taken together is effective to reduce a clinical symptom of the Mtb infection in the subject.

In some embodiments, the subject is also afflicted with an immunodeficiency disorder. In some embodiments, the subject is also afflicted with human immunodeficiency virus (HIV).

In some embodiments, a pharmaceutical composition comprising an amount of the compound of the present invention for use in treating a subject afflicted with tuberculosis as an add-on therapy or in combination with, or simultaneously, contemporaneously or concomitantly with an anti-tuberculosis agent.

In some embodiments of any of the above methods or uses, the compound and anti-tuberculosis agent are orally administered to the subject.

In some embodiments, the tuberculosis infection has developed resistance to one or more drugs. For example, a drug resistant tuberculosis infection may have developed drug-resistance to a first line TB drug such as, for example, isoniazid, rifampicin, pyrazinamide, ethambutol or streptomycin.

The chemical linker may be cleavable, non-cleavable or a releasable linker.

In some embodiments, the chemical linker is a cleavable linker.

The term "cleaveable linker" is intended to mean a moiety that is unstable in vivo. The linker may be cleaved in vivo by the biological environment. The cleavage may come from any process without limitation, e.g., enzymatic, reductive, pH, etc. The cleaveable group may be selected so that activation occurs at the desired site of action, which can be a site in or near the target cells (e.g., bacteria cells).

The cleavable linker can be cleaved from the azasteroid core by, for example, enzymatic cleavage in vivo, to release the anti-tuberculosis drug. The compound may bind to a cell and become internalized prior to the anti-tuberculosis drug being enzymatically released to become activated inside the cell. Examples of the linker include, but are not limited to, heteroaryl linkers, peptide linkers, self-immolative linkers, disulfide linkers, thioether linkers, hydrazine linkers, maleimide linkers, hydrophilic linkers or other linkers that are generally known in the art.

In some embodiments, the chemical linker comprises a disulfide bond.

In some embodiments, the chemical linker comprises a

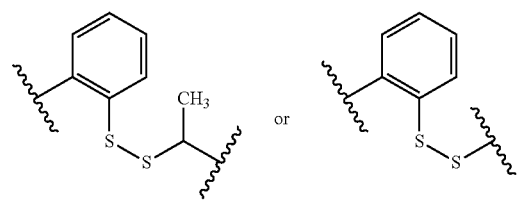 [SMILES: *c1ccccc1SSC(*)C ; *SSc1ccccc1*]

group.

In some embodiments, the linker has the structure:

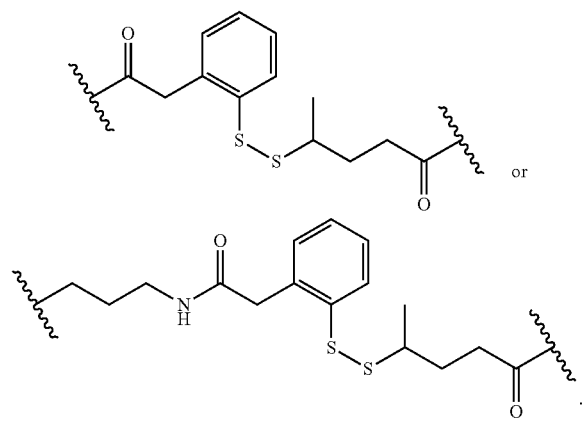

In some embodiments, the L-(anti-tuberculosis drug) has the structure:

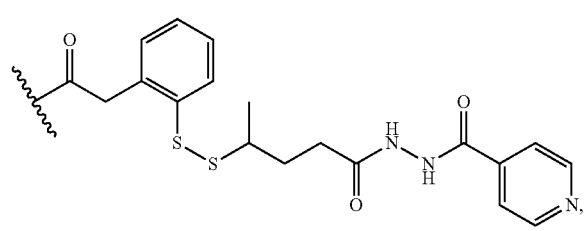

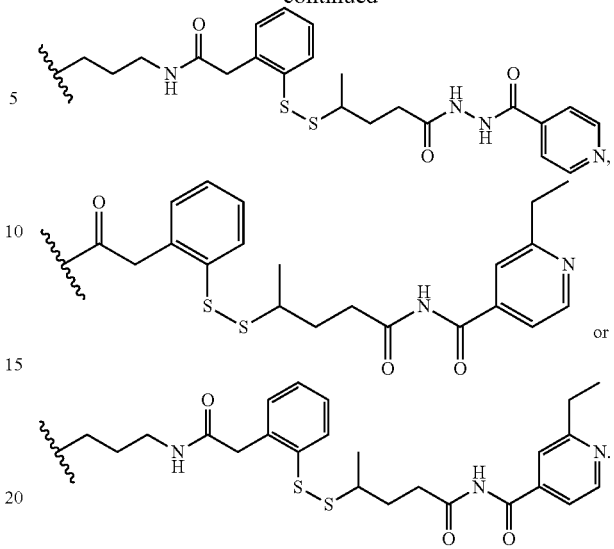

In some embodiments, the cleavable linker is cleavable in the presence of bacteria cells.

In some embodiments, the cleavable linker is cleavable in bacteria cells.

In some embodiments, the cleavable linker is cleavable in mammalian cells.

The subject invention also provides a pharmaceutical composition comprising an amount of the compound of the present invention for use in treating a subject infected with *M. tuberculosis* as an add-on therapy or in combination with an anti-tuberculosis drug.

The subject invention also provides a pharmaceutical composition comprising an amount of the compound of the present invention for use in treating a subject infected with *M. tuberculosis* simultaneously, contemporaneously or concomitantly with an anti-tuberculosis drug.

The subject invention also provides a pharmaceutical composition comprising an amount of an anti-tuberculosis drug for use treating a subject infected with *M. tuberculosis* as an add-on therapy or in combination with the compound of the present invention.

The subject invention also provides a pharmaceutical composition comprising an amount of an anti-tuberculosis drug for use treating a subject infected with *M. tuberculosis* simultaneously, contemporaneously or concomitantly with the compound of the present invention.

The subject invention also provides the compound of the present invention for use as an add-on therapy or in combination with an anti-tuberculosis drug in treating a subject infected with *M. tuberculosis*.

The subject invention also provides an anti-tuberculosis drug for use as an add-on therapy or in combination with the compound of the present invention in treating a subject infected with *M. tuberculosis*.

The combination of the invention may be formulated for its simultaneous, separate or sequential administration, with at least a pharmaceutically acceptable carrier, additive, adjuvant or vehicle. The combination of the two active compounds may be administered as a combination that is part of the same medicament formulation or as a combination of two units, each with one of the active substances.

The administration of two drugs to treat a given condition, such as *M. tuberculosis* infection, raises a number of potential problems. In vivo interactions between two drugs are complex. The effects of any single drug are related to its absorption, distribution, metabolism, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug (Guidance for Industry, 2012). Thus, when two drugs are administered to treat the same condition, it is unpredictable whether each will complement, have no effect on, or interfere with, the therapeutic activity of the other in a subject.

In some embodiments of any of the above methods or uses, the subject is instead infected with *Mycobacteria* spp., *Nocardia* spp., *Rhodococcus* spp., *N. asteroids* complex, *M. avium* complex, *Rhodococcus equi*. and the compound is used to treat the subject.

In some embodiments of any of the disclosed methods, the anti-tuberculosis drug is Isoniazid (H/Inh), Rifampicin (R/Rif), Pyrazinamide (Z/Pza), Ethambutol (E/Emb) or Streptomycin (S/Stm).

In some embodiments of any of the disclosed methods, the anti-tuberculosis drug is a fluoroquinolone.

In some embodiments of any of the disclosed methods, the anti-tuberculosis drug is a second line injectable agent.

In some embodiments of any of the disclosed methods, the anti-tuberculosis drug is Amikacin (Am), Capreomycin (Cm), Kanamycin (Km) or (Streptomycin).

In some embodiments of any of the disclosed methods, the anti-tuberculosis drug is a core second line agent.

In some embodiments of any of the disclosed methods, the anti-tuberculosis drug is an Ethionamide/Prothionamide (Eto/Pto) combination or a Cycloserine/Terizidone (Cs Trd) combination.

In some embodiments of any of the disclosed methods, the anti-tuberculosis drug is an add-on agent.

In some embodiments of any of the disclosed methods, the anti-tuberculosis drug is Pyrazinamide, Ethambutol (E), High-dose isoniazid (Hh), Bedaquiline (Bdq), Delamanid (Dlm), p-aminosalicylic acid (PAS), lmipenem-cilastatin (lpm), Meropenem (Mpm), Amoxicillin-clavulanate (Amx-Clv) or Thioacetazone (T).

In some embodiments of any of the disclosed methods, the anti-tuberculosis drug is Q203-Novel anti-TB agent, Sutezolid (PNU-100480), SQ109 or Rifapentine.

In some embodiments of any of the disclosed methods, the anti-tuberculosis drug is a combination of one or more anti-tuberculosis drugs disclosed herein.

In some embodiments of any of the disclosed methods, the anti-tuberculosis drug is a combination of two anti-tuberculosis drugs disclosed herein.

In some embodiments of any of the disclosed methods, the anti-tuberculosis drug is a combination of three anti-tuberculosis drugs disclosed herein.

As used herein, a "symptom" associated with TB includes any clinical or laboratory manifestation associated with the infection and is not limited to what the subject can feel or observe.

As used herein, "treating", e.g. of TB, encompasses inducing prevention, inhibition, regression, or stasis of the disease or a symptom or condition associated with the infection.

The compounds of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention.

The compounds of the subject invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms. However, it is understood that enough hydrogen atoms exist on said carbon atoms to satisfy the octet rule.

This invention also provides isotopic variants of the compounds disclosed herein, including wherein the isotopic atom is $^2$H and/or wherein the isotopic atom $^{13}$C. Accordingly, in the compounds provided herein hydrogen can be enriched in the deuterium isotope. It is to be understood that the invention encompasses all such isotopic forms.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, N Y, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14. Isotopes of nitrogen include N-15.

It will be noted that any notation of a carbon in structures throughout this application, when used without further notation, are intended to represent all isotopes of carbon, such as $^{12}$C, $^{13}$C, or $^{14}$C. Furthermore, any compounds containing $^{13}$C or $^{14}$C may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

It will also be noted that any notation of a nitrogen in structures throughout this application, when used without further notation, are intended to represent all isotopes of nitrogen, such as $^{19}N$ or $^{15}N$. Furthermore, any compounds containing $^{15}N$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano, carbamoyl and aminocarbonyl and aminothiocarbonyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n–1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2 . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl, $C_3$-$C_{12}$ alkenyl, $C_4$-$C_{12}$ alkenyl and so on.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl, $C_3$-$C_{12}$ alkynyl, $C_4$-$C_{12}$ alkynyl and so on "Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "heteroalkyl" includes both branched and straight-chain saturated aliphatic hydrocarbon groups having the specified number of carbon atoms and at least 1 heteroatom within the chain or branch.

As herein, "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

The term "arylalkyl" refers to alkyl groups as described above wherein one or more bonds to hydrogen contained therein are replaced by a bond to an aryl group as described above. It is understood that an "arylalkyl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle" or "heterocyclyl" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The alkyl, alkenyl, alkynyl, aryl, heteroaryl and heterocyclyl substituents may be substituted or unsubstituted, unless specifically defined otherwise. In the compounds of the present invention, alkyl, alkenyl, alkynyl, aryl, heterocyclyl and heteroaryl groups can be further substituted by replacing one or more hydrogen atoms with alternative non-hydrogen groups. These include, but are not limited to, halo, hydroxy, mercapto, amino, carboxy, cyano and carbamoyl.

As used herein, the term "halogen" refers to F, Cl, Br, and I.

The terms "substitution", "substituted" and "substituent" refer to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or pluraly. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) $5^{th}$ Edition (1996), March's Advanced Organic Chemistry: Reactions, Mechanisms, and Structure, Michael B. Smith, Jerry March, (Wiley-Interscience) $5^{th}$ Edition (2007), and references therein, which are incorporated by reference herein. However, these may not be the only means by which to synthesize or obtain the desired compounds.

Another aspect of the invention comprises a compound used in the method of the present invention as a pharmaceutical composition.

In some embodiments, a pharmaceutical composition comprising the compound of the present invention and a pharmaceutically acceptable carrier.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, 30$^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed.

Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The compounds of the present invention may also form salts with basic amino acids such a lysine, arginine, etc. and with basic sugars such as N-methylglucamine, 2-amino-2-deoxyglucose, etc. and any other physiologically non-toxic basic substance.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier as are slow-release vehicles.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antitumor agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or topically onto a site of disease or lesion, all using dosage forms well known to those of ordinary skill in the pharmaceutical arts.

The compounds used in the method of the present invention can be administered in admixture with suitable pharmaceutical diluents, extenders, excipients, or in carriers such as the novel programmable sustained-release multi-compartmental nanospheres (collectively referred to herein as a pharmaceutically acceptable carrier) suitably selected with respect to the intended form of administration and as consistent with conventional pharmaceutical practices. The unit will be in a form suitable for oral, nasal, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamellar vesicles, and multilamellar vesicles. Liposomes can be formed from a variety of phospholipids such as lecithin, sphingomyelin, proteolipids, protein-encapsulated vesicles or from cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials such as solutol and/or ethanol to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutically acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described—in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric-coated to prevent release of the active ingredient compounds before they reach the small intestine. Materials that may be used as enteric coatings include, but are not limited to, sugars, fatty acids, proteinaceous substances such as gelatin, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers.

The compounds and compositions of the invention can be coated onto stents for temporary or permanent implantation into the cardiovascular system of a subject.

Variations on those general synthetic methods will be readily apparent to those of ordinary skill in the art and are deemed to be within the scope of the present invention.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Bacterial Strains and Culture Conditions.
*M. tuberculosis* strains CDC1551, H37Rv and Erdman (ATCC 35801) were cultured at 37° C. in Middlebrook 7H9 (broth) supplemented with 0.2% glycerol or 0.1 mM cholesterol, 0.5% BSA, 0.08% NaCl, 0.05% (v/v) tyloxapol or 7H11 (agar) supplemented with 10% oleate-albumin-dextrose-NaCl (OADC), 0.5% glycerol, 0.05% Tween 80.

Determination of Minimal Inhibitory Concentration (MIC).
MIC values were determined by broth microdilution assay (De Voss, J. J. et al. 2000).
Briefly, cells were grown to an $OD_{600}$ of 0.2, diluted 1000 fold in defined media. Cell suspension was added to a 96-well plate containing compound dilutions to obtain a final volume of 100 µL. Plates were incubated at 37° C. for 10-14 days and MIC was determined as the lowest concentration that resulted in complete inhibition of growth.

Low Oxygen Recovery Assay (LORA).
*M. tuberculosis* constitutively expressing the luxABCDE operon was inoculated into DTA medium in gas-impermeable glass tubes and incubated for 18 days to generate hypoxic conditions (Wayne model of hypoxia) (Cho, S. H. et al. 2007; Wayne, L. G. et al. 2001; Andreu, N. et al. 2010). Test compounds were prepared as 20-point two-fold serial dilutions in DMSO and diluted into DTA medium in 96-well plates with a final DMSO concentration of 2%. Oxygen-deprived bacteria were inoculated into compound assay plates and incubated under anaerobic conditions for 10 days followed by incubation under aerobic conditions (outgrowth) for 28 h. Growth was measured by luminescence. Rifampicin was included as a positive control.

Determination of Minimum Bactericidal Concentration (MBC).
*M. tuberculosis* was grown log phase and inoculated into liquid medium containing different compound concentrations at 10×MIC, 5×MIC, 1×MIC, and 0.25×MIC. Cultures were exposed to compounds for 21 days and cell viability measured by enumerating colony forming units (CFU) on agar plates on day 0, 7, 14 and 21. MBC was defined as the minimum concentration required to achieve a 2-log kill in 21 days.

Time-Kill Assay.
Bacteria were grown at 37° C. to mid-log phase and then diluted in 10 mL fresh media to a 5×10 CFUs/mL. Compounds were added at defined concentrations. Aliquots of cultures were withdrawn at specified time points, and OD600 were recorded. At 0, 7 and 14 days, aliquots of cultures were serially diluted in 7H9 broth and plated on 7H11/OADC agar plates. Plates were incubated at 37° C. and CFUs were counted after 3 to 4 weeks.

Cytotoxicity Assay.
The cytotoxicity of SB107 was determined by measuring hERG, THP-1, HepG2, and HK-2 cell viability after 3 days in the presence of SB107 in a 384-well plate format. SB107 was prepared as 10-point serial dilutions in DMSO, with the highest concentration at 30 µM. Assay plates were incubated for 3 days at 37° C., 5% $CO_2$ and relative luminescent units (RLU) were measured using the CellTiter-Glo® Luminescent Cell Viability Assay. The dose response curve was fitted using the Levenberg-Marquardt algorithm. The $IC_{50}$ was defined as the compound concentration that resulted in 50% viability.

Intracellular Activity Assay.
The activity of compounds against intracellular bacteria was determined by measuring viability in infected J774A.1 cells after 3 days in the presence of test compounds. J774A.1 cells were cultured in DMEM supplemented with 10% FBS, 4 mM L-glutamine, and 1 mM sodium pyruvate in a humidified incubator at 37° C. and 5% $CO_2$. Cells were infected with a luminescent strain of H37Rv (which constitutively expresses luxABCDE) at a multiplicity of infection of ~10 at 37° C., 5% $CO_2$, in 96-well plates. After 20 h infection, different drugs or an equivalent amount of DMSO were added to the infected cells. After 72 h of treatment, relative luminescent units (RLU) were measured. The dose response curve was fitted using the Levenberg-Marquardt algorithm. The $IC_{50}$ and $IC_{90}$ were defined as the compound concentrations that produced 50% and 90% inhibition of bacterial growth respectively. All samples were analyzed in triplicate.

Frequency of Resistance.

*M. tuberculosis* mutants resistant to 114 or 100 were isolated as previously described by Ioerger et al. (Ioerger, T. R. et al. 2013). *M. tuberculosis* H37Rv bacteria were grown at 37° C. to mid-log phase and then diluted in fresh Middlebrook 7H9 medium-ADC-Tween 80 to $5 \times 10^8$ CFU/mL. Middlebrook 7H11/OADC agar plates with 114 or 100 at 5×MIC or 10×MIC with or without the addition of 10×MIC bedaquiline were inoculated with $10^8$, $10^7$, $10^6$, and $10^5$ CFU/plate, and the plates were incubated at 37° C. for 3 to 4 weeks. Resistance was confirmed by measuring the MIC. The frequency of the appearance of resistant mutants was calculated.

Metabolic Stability in Human Liver Microsomes.

100, 107, 114 at the concentration of 2 μM were incubated with human liver microsomes (mixed-gender pool, Corning) at the concentration of 0.5 mg/mL at 37° C. for 1 hour in phosphate buffer (pH 7.4) with or without 1 mM NADPH. Aliquots of the reaction solution were withdrawn at 0, 15, 30, 45 and 60 minutes, extracted with acetonitrile containing appropriate internal standards (IS). The concentration of the parent compound was determined by LC-MS/MS analysis. Verapamil was used as a positive control.

Inhibition of CYPs.

The potential for inhbition of CYP enzymes (CYP1A2, CYP2A6, CYP2B6, CYP2C8, CYP2C9, CYP2C19, CYP2D6, CYP2E1 and CYP3A4) by 107 at 10 μM were using pooled male and female human liver microsomes, Freshly plated human microsomes with substrate to each CYP enzyme was treated with 107 for 5-20 min. The concentrations of marker metabolites of known substrates were determined by LCMS analysis.

Caco-2 Permeability Assay.

Caco-2 cells were diluted to $6.86 \times 10^6$ cells/mL, dispensed into a 96-well HTS Transwell plate, and cultured for 14 to 18 days. 6-azasteroids at 5 μM was incubated at 37° C. for 2 hours with the Caco-2 cell monolayer in HBSS buffer (10 mM HEPES, pH 7.4) containing 5% BSA. Aliquots from donor sides (apical compartment for Ap→Bl flux, and basolateral compartment for Bl→Ap) and receiver sides (basolateral compartment for Ap→Bl flux, and apical compartment for Bl→Ap) were separated and extracted by acetonitrile or methanol containing appropriate internal standards (IS). The concentration of 6-azasteroid was determined by LC-MS/MS analysis.

HERG Assay.

hERG stably expressed HEK 293 cells were seeded at $5 \times 10^5$ cells/per 6 cm cell culture dish and induced with doxycycline at 1 μg/mL for 48 hours. Compound at the final concentrations of 30, 10, 3.33, 1.11 and 0.37 μM was applied to the cells accumulatively, post-compound hERG currents were recorded, and $IC_{50}$ was calculated. Dofetilide was used as a positive control.

Pharmacokinetic (PK) and Bioavailability of 107

Male CD-1 mice were dosed intravenously (1 mg/kg) and orally (5 mg/kg) with 107 that is formulated in 30% Solutol. After dosing, blood samples were collected at different time points (5, 15, 30 min, 1, 2, 4, 6, 8 and 24 hours) for each group. Compound concentrations in plasma samples were analyzed by liquid chromatography-tandem mass spectrometry (LC-MS/MS).

Lung Tissue Distribution of 107

Male CD-1 mice were dosed intravenously (1 mg/kg) and orally (5 mg/kg) with 107 that is formulated in 30% Solutol. Lung samples were collected at different time points (5, 15, 30 min, 1, 2, 4, 6, 8 and 24 hours) post dosing. All of the lungs were weighed and homogenized by water before analysis. Drug concentrations in each sample were analyzed by LC-MS/MS.

LC/MS/MS Analysis.

To measure the concentrations of 100, 107 and 114 in the human liver microsomal stability assay, Caco-2 permeability assay and pharmacokinetic analysis, an HPLC (Shimadzu) connected to an API 5500 instrument (AB Inc, Canada) with an ESI interface was used. A Phenomenex Kinetex C18 column (1.7 μm, 100 A, 30*2.1 mm) was eluted with Phase A: water (0.1% FA) and Phase B: ACN (0.1% FA), 0-0.8 min, 5-100% B; 0.8-1.1 min, 100% B; 1.1-1.2 min, 100-5% B; 1.2-1.4 min, 5% B. Injection volume: 3 μL. Elution rate: 0.65 mL/min. 100, 107 and 114 were monitored by positive multiple reaction monitoring mode at the transition of m/z 506 to 448, 687 to 631 and 548 to 300, respectively.

Example 1. Synthesis of 6-Azasteroid Compounds

Scheme 1.

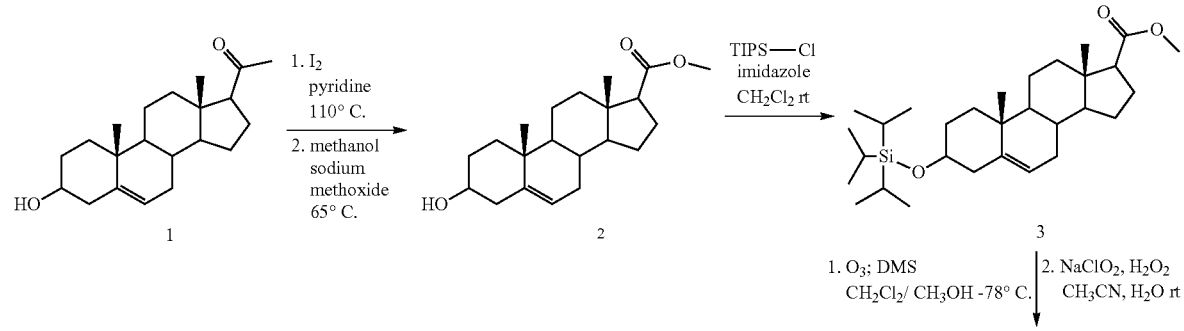

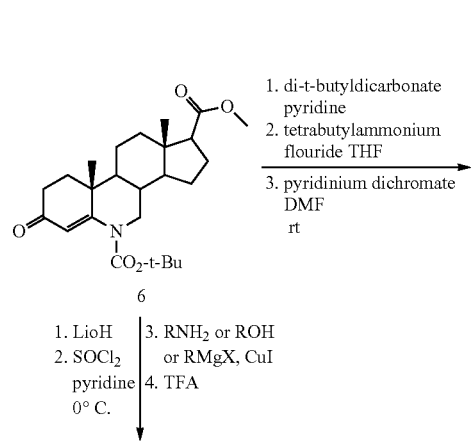

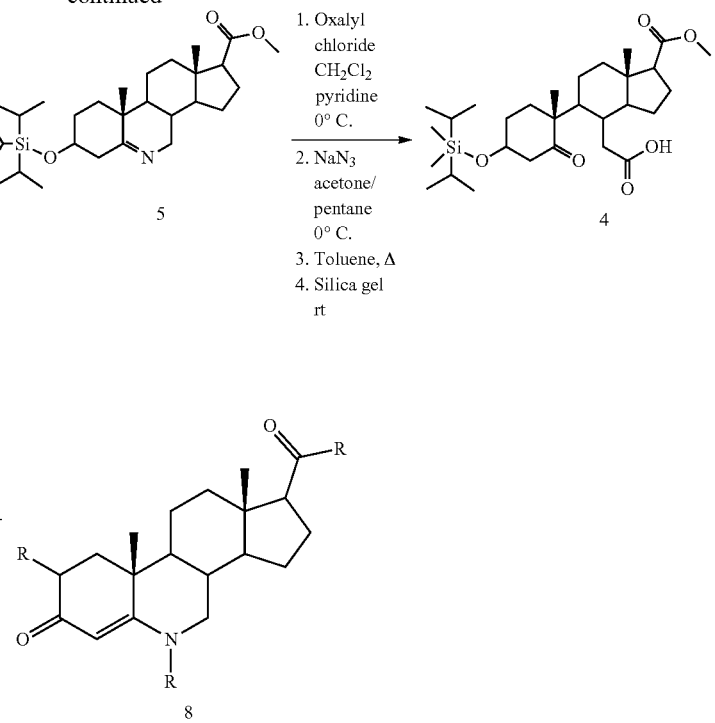

3β-Hydroxyetienic Acid Methyl Ester (2)

Iodine (43 g, 0.17 mol) was added portionwise over 15-30 min to an initially warm (90° C.) solution of pregnenolone (50 g, 0.16 mol) in 125 mL of pyridine. The reaction was heated to reflux during addition and was stirred for an additional 90 min while the temperature remained above 100° C. The mixture was cooled gradually to rt and was filtered. The solid was washed three times with 100 mL of pyridine and twice with 100 mL of diethyl ether. Air-drying gave a 59.4 g (yield: 74%) of crude pregnenolone 21-pyridinium iodide as a yellow-tan powder. The crude pyridinium iodide (59.4 g) was added into a refluxing solution of sodium methoxide (7.18 g) in 125 mL of MeOH over 15 min. The heavy slurry gradually dissolved and the dark solution was refluxed for another an hour. Upon cooling to rt, the ester crystallized. Water (125 mL) was added with vigorous stirring followed by neutralization with 10 mL of 6 M HCl solution. After stirring for 1 h, the solid was removed by filtration and was washed four times with 150 mL of 1:1 MeOH/water until the color was largely extracted. The brown color solid was dried in air. 37.5 g of 2 were collected, yield 97% (Rasmusson, G. H. et al. 1984).

3β-triisopropylsilyloxyetienic Acid Methyl Ester (3)

The 3β-hydroxyetienic acid methyl ester (18 g 0.054 mol) and imidazole (9 g 0.132 mol) was dissolved in 30 mL of CH$_2$Cl$_2$. Triisopropylsilylcholoride (12 g 0.062 mol) was added dropwise to the mixture at 0° C. with vigorous mechanical stirring. The reaction was complete by TLC (10% ethyl acetate/hexane) after 48 h. The mixture was cooled to 0° C. and 50 mL of ice water was added. Rotary evaporation was used to remove CH$_2$Cl$_2$. The solid was suspended in methanol (50 mL) and stirred for 16 h to give, on filtration, 3β-triisopropylsilyloxyetienic acid methyl ester as a tan solid. Flash chromatography (2% ethyl acetate/hexane) provided 3 as a white solid, 22.7 g, yield 85.6% (Frye, S. V. et al. 1993).

Keto-Acid (4)

8.0 g of purified alkene, 3, was dissolved in 300 mL CH$_2$Cl$_2$ and 100 mL MeOH. The solution was cooled to −78° C. and treated with ozone until the reactant disappeared on TLC. When the reaction was warmed to rt, 12 mL of DMS was added into the reaction with stirring for 16 h. The solvents were removed. The solid mixtures were dissolved in 50 mL of CH$_3$CN. The solution was treated with 1.2 mL H$_2$O$_2$ 30% solution, then with 70 mL aqueous sodium chlorite (2.0 g) at 0° C. and stirred for 16 h. Flash chromatography (15% ethyl acetate/hexane) provided the keto-acid, 4, as white solid, 7.4 g, 84% yield (Frye, S. V. et al. 1993).

17β-Carbomehoxy-3β-triisopropylsilyloxy-6-azaandrost-5-ene (5)

Keto-acid (600 mg, 1.12 mmol) was dissolved in CH$_2$Cl$_2$ (0.8 mL) and pyridine (0.3 mL) and added dropwise to a solution of oxalyl chloride (0.24 mL, 2.8 mmol, 2.5 eq) in CH$_2$Cl$_2$ (4.2 mL) at 0° C. After stirring for 1 h, the reaction mixture was poured into a mixture of aqueous NaCl and ice (10 mL). The organic layer was washed with ice-cold 0.5 M HCl (2*10 mL), ice-cold saturated NaHCO$_3$ (2*10 mL), dried with Na$_2$SO$_4$ and concentrated to obtain the acyl chloride. The acyl chloride was dissolved in acetone (6 mL) and pentane (0.3 mL) at 0° C. and treated with aqueous sodium azide (0.3 g, 4.6 mmol, 4 eq, 1.5 mL). After stirring 60 min, the solution was poured in to a mixture of brine, saturated NaHCO$_3$ and ice (5 mL*3). Toluene (10 mL) was added into the mixture and the organic layer was washed with saturated NaHCO$_3$ three times (10 mL*3), dried with Na$_2$SO$_4$ and heated to 110° C. to distill off half of the volume. When the solution was cooled to rt, silica gel (1.6 g) was added and the reaction was stirred for 18 h. The silica gel was removed by filtration and washed with 4:1 ethyl acetate/MeOH. Rotary evaporation provided the crude 17β-Carbomehoxy-3β-triisopropylsilyloxy-6-azaandrost-5-ene, 5, as dark brown solid. Flash chromatography using 20% ethyl acetate/hexane provided 5 as white solid (Frye, S, V. et al. 1993).

17β-Carbomethoxy-6-t-butoxycarbonyl-6-azaandrost-4-en-3-one (6)

The purified 5 (3 g, 0.006 mol) was dissolved in pyridine (25 mL), and di-t-butyldicarbonate (4 g, 0.018 mol) were added to the solution with stirring for 16 h at rt. The pyridine was removed by rotary evaporation and the residue was dissolved in tetrabutylammonium fluoride in THF solution (25 mL, 1 M). The solution was heated to reflux for 5 min and concentrated. The residue was dissolved in ethyl acetate (25 mL), washed with water, brine, and dried with MgSO$_4$ and concentrated. Chromatography gave the desilylated compound as white solid. The desilylated compound was dissolved in DMF (25 mL) and treated with pyridinium dichromate (6.8 g, 0.018 mol). After stirring 16 h, ethyl acetate (25 mL) was added to the solution. The organic layer was separated and washed with water, 5% CuSO$_4$ solution and brine, and dried with MgSO$_4$. The solution was filtered through a short packed silica gel column to further remove chromium. Flash chromatography (15% ethyl acetate/hexane) provided 6 as white solid (Frye, S, V. et al. 1993).

17β-Carboxy-6-t-butoxycarbonyl-6-azaandrost-4-en-3-one

A solution of 6 (50 mg) in dioxane (1.5 mL) and H$_2$O (1 mL) was treated with lithium hydroxide (6 mg, 2 eq) and stirred 16 h at 70° C. The reaction mixture was poured into saturated aqueous NaHSO$_4$ solution (10 mL) and extracted with CH$_2$Cl$_2$ three times. The extracts were washed with brine and dried over MgSO$_4$. Chromatography using 5% methanol in CH$_2$Cl$_2$ gave the carboxylic acid as white powder (Frye, S, V. et al. 1993).

General Procedure for the C-17 Coupling and Deprotection (7)

30 mg of 17β-Carboxy-6-t-butoxycarbonyl-6-azaandrost-4-en-3-one was suspended in 1 mL of toluene. One drop of DMF and 15 μL of pyridine were added into the solution. Under ice bath, the solution was treated with 10 μL of thionyl chloride followed by stirring for 1 h. The solution was filtered, concentrated and dissolved in DCM. The acid chloride was treated with appropriate amine to give the tBoc-amide. The tBoc-amide was dissolved in DCM and treated with 2 mL of TFA. After 2 h, the reaction was poured into saturated NaHCO$_3$ solution and the organic layer was washed with brine and dried over Na$_2$SO$_4$. Chromatography using 5% methanol in DCM gave the deprotected amide, 7 (Frye, S, V. et al. 1993).

General Procedure for N-6 Alkylation (8)

30 mg of the compound 7 was dissolved in DMF and treated with 1.2 eq of NaH. After stirring for 30 min, the reaction was treated with appropriate iodoalkane for further 30 min. When the reaction was complete, 30 mL of ethyl acetate was added and the solution was washed with water and brine for three times, dried over Na$_2$SO$_4$. Chromatography using 5% isopropanol in DCM gave the N-6 alkylated amide (Frye, S, V. et al. 1993).

The above methods were used to synthesize compounds 100, 101, 103-105, 107, 109, and 112-114. The H$^1$-NMR spectra of 100, 103-105, 107, 109, and 112-114 are summarized below:

100: $^1$H NMR (500 MHz, Chloroform-d) δ 8.14 (s, 1H), 7.78 (s, 1H), 7.30 (d, J=8.4 Hz, 1H), 7.13 (d, J=6.1 Hz, 2H), 5.57 (s, 1H), 3.51 (dd, J=13.2, 6.0 Hz, 1H), 3.00 (t, J=12.2 Hz, 1H), 2.48 (dd, J=13.0, 5.3 Hz, 1H), 2.34 (d, J=3.7 Hz, 3H), 2.25 (d, J=11.5 Hz, 1H), 2.08-1.89 (m, 3H), 1.69 (dh, J=18.6, 6.0, 5.4 Hz, 3H), 1.40 (s, 13H), 1.31 (s, 16H), 0.92 (s, 3H).

103: $^1$H NMR (500 MHz, Chloroform-d) δ 8.76 (s, 1H), 7.73 (d, J=8.3 Hz, 1H), 7.54-7.40 (m, 2H), 5.81 (s, 1H), 4.30 (dd, J=12.6, 4.5 Hz, 1H), 2.68-2.24 (m, 5H), 2.14 (d, J=11.2 Hz, 1H), 2.08-2.00 (m, 1H), 1.99-1.73 (m, 4H), 1.65 (td, J=14.0, 4.6 Hz, 2H), 1.44 (s, 12H), 1.23 (d, J=22.9 Hz, 10H), 0.87 (q, J=6.7 Hz, 2H), 0.84 (s, 3H).

104: $^1$H NMR (500 MHz, Chloroform-d) δ 7.45 (dd, J=8.6, 5.8 Hz, 1H), 7.37-7.28 (m, 1H), 6.92 (d, J=2.3 Hz, 1H), 6.83 (d, J=2.3 Hz, 0H), 5.59 (d, J=25.0 Hz, 1H), 3.27 (dd, J=13.0, 6.3 Hz, 1H), 3.19 (s, 2H), 3.10 (s, 1H), 2.90 (s, 3H), 2.57-2.32 (m, 2H), 2.23 (d, J=3.6 Hz, 1H), 2.12-1.66 (m, 5H), 1.37 (s, 3H), 1.34-1.17 (m, 21H), 1.17-0.93 (m, 4H), 0.90 (s, 5H).

105: $^1$H NMR (400 MHz, Chloroform-d) δ 11.18 (s, 3H), 10.30 (s, 1H), 8.77 (s, 1H), 7.10 (s, 1H), 6.10 (s, 1H), 3.95 (s, 3H), 3.66 (d, J=11.4 Hz, 1H), 3.15 (s, 1H), 2.75-2.22 (m, 5H), 2.22-1.84 (m, 5H), 1.84-1.60 (m, 3H), 1.60-1.15 (m, 11H), 0.80 (s, 3H).

107: $^1$H NMR (500 MHz, Chloroform-d) δ 8.86 (s, 1H), 6.98 (s, 1H), 5.81 (s, 1H), 4.30 (dd, J=12.6, 4.5 Hz, 1H), 3.94 (s, 3H), 2.65-2.22 (m, 6H), 2.04 (s, 4H), 1.96-1.71 (m, 4H), 1.71-1.58 (m, 3H), 1.44 (s, 13H), 1.23 (d, J=25.3 Hz, 9H), 0.79 (s, 3H).

109: $^1$H NMR (500 MHz, Chloroform-d) δ 7.41 (d, J=1.7 Hz, 2H), 7.34 (s, 1H), 7.17 (s, 1H), 6.37 (s, 1H), 5.23 (s, 1H), 3.39 (ddd, J=12.3, 5.8, 2.3 Hz, 1H), 2.91 (t, J=11.7 Hz, 1H), 2.46 (ddd, J=18.4, 13.4, 5.4 Hz, 1H), 2.39-2.26 (m, 3H), 2.19-2.07 (m, 1H), 2.07-1.92 (m, 2H), 1.84 (dtd, J=13.1, 10.0, 9.1, 5.0 Hz, 1H), 1.66 (ddd, J=18.7, 11.2, 7.4 Hz, 3H), 1.47 (qd, J=13.1, 5.2 Hz, 2H), 1.31 (s, 28H), 0.83 (s, 3H).

112: $^1$H NMR (500 MHz, Chloroform-d) δ 7.48 (d, J=8.6 Hz, 3H), 7.32 (d, J=8.7 Hz, 2H), 5.30 (s, 1H), 3.40 (ddd, J=12.8, 5.9, 2.4 Hz, 1H), 2.91 (t, J=11.8 Hz, 1H), 2.46 (ddd, J=18.3, 13.3, 5.4 Hz, 1H), 2.40-2.24 (m, 3H), 2.13-1.90 (m, 3H), 1.84 (qd, J=12.0, 11.0, 7.8 Hz, 1H), 1.64 (t, J=5.1 Hz, 3H), 1.43 (d, J=9.5 Hz, 2H), 1.28 (d, J=7.3 Hz, 17H), 0.80 (s, 3H).

113: $^1$H NMR (500 MHz, Chloroform-d) δ 7.78 (d, J=2.3 Hz, 1H), 7.30 (d, J=8.4 Hz, 1H), 7.17-7.08 (m, 2H), 5.27 (s, 1H), 3.31 (dd, J=12.3, 5.9 Hz, 1H), 3.26-3.08 (m, 1H), 2.86 (s, 4H), 2.33 (d, J=8.2 Hz, 6H), 2.15-1.87 (m, 4H), 1.86-1.60 (m, 4H), 1.40 (s, 14H), 1.29 (d, J=16.7 Hz, 20H), 0.92 (s, 3H), 0.90-0.81 (m, 2H).

114: $^1$H NMR (500 MHz, Chloroform-d) δ 7.80 (d, J=2.3 Hz, 1H), 7.32 (d, J=8.4 Hz, 1H), 7.16 (d, J=6.5 Hz, 2H), 3.46-2.76 (m, 5H), 2.36 (d, J=8.4 Hz, 6H), 2.16-1.92 (m, 4H), 1.70 (dd, J=14.7, 7.7 Hz, 6H), 1.43 (s, 13H), 1.37-1.19 (m, 22H), 0.98 (s, 3H), 0.94 (s, 5H).

Example 2. Isoniazid MIC Shift of 6-Azasteroid Compounds

Compounds 100, 101, 103-105, 107, 109, and 112-114 in combination with isoniazid were tested using Mtb MIC plates. The compound was held at a fixed concentration between 10 and 20 μM and the isoniazid concentration was administered to the plate at a molar ratio varying from 2:1 to 1000:1 compound:isoniazid. Compounds 100, 101, 103-105, 107, 109, and 112-114 decreased the amount of isoniazid needed to inhibit growth of bacterial isolates, see Table 1. The MIC for isoniazid alone was 0.2-0.4 μM. Compound alone did not completely inhibit growth.

TABLE 1

Isoniazid MIC shift @ 20 μM of compound

| COMPOUND | Isoniazid MIC shift |
| --- | --- |
| 101 | +++ |
| 100 | +++ |
| 103 | +++ |
| 113 | +++ |
| 114 | +++ |
| 104 | ++ |
| 107 | ++ |
| 109 | ++ |
| 105 | + |

(2-4-fold +, 4-8-fold ++, >10-fold +++)

The screening was performed with a single concentration of 6-azasteroid and the potentiation potency was recorded as a fold change of isoniazid MIC. The compounds listed in Table 1 were found to shift the MIC of isoniazid and therefore identified as potentiators to improve the efficacy of isoniazid using either cholesterol or glycerol as a carbon source. Active compounds were further examined by checkerboard assay, with varied concentrations of both isoniazid and 6-azasteroid. The fractional inhibitor index (FIC) for INH/114 is 0.31-0.56.

Example 3. 6-Azasteroids are Active with Additional Anti-TB Drugs 100 and 114 were tested with other existing TB drugs including pretomanid, rifampin, ethionamide, bedaquiline, linezolid, clofazamine, moxifloxicin and pyrazinamide. It was discovered that 6-azasteroids potentiate the activity of at least 3 additional TB drugs: bedaquiline, ethionamide, and pretomanid (Table 2). The fractional inhibitory constant for BDQ/114 is 0.27-0.52.

TABLE 2

In vitro potentiation of 20 μM 6-azasteroid with isoniazid (INH) against M. tuberculosis CDC1551 using cholesterol as a carbon source.

| Compound mixture[a] | Aerobic MIC (μM) |
| --- | --- |
| INH | 0.2-0.4 |
| INH with 20 μM 100, 107 or 114 | 0.0013 |
| INH with 10 μM 100 | 0.025 |
| BDQ | 0.1 |
| BDQ with 10 μM 100 | 0.01 |
| BDQ with 10 μM 114 | <0.0015 |
| ETH | 12.5 |
| ETH with 10 μM 100, 104 or SB105 | <0.05 |
| Pa | 0.00625 |
| Pa with 10 μM 100 or 105 | 0.0002 |
| CLOF | 2 |
| CLOF with 10 μM 100 or 114 | NC[b] |
| LIN | 0.8 |
| LIN with 10 μM 100 or 114 | NC |

TABLE 2-continued

In vitro potentiation of 20 μM 6-azasteroid with isoniazid (INH) against M. tuberculosis CDC1551 using cholesterol as a carbon source.

| Compound mixture[a] | Aerobic MIC (μM) |
| --- | --- |
| MOXI | 0.18 |
| MOXI with 10 μM 100 or 114 | NC |

[a]Testing was performed in CDC1551, H37Rv and H37Rv(luxAB).
[b]INH: isoniazid; BDQ: bedaquiline; ETH: ethionamide; Pa, pretomanid; CLOF: clofazimine; LIN: linezolid; MOXI: moxifloxacin
[b]NC: No Change in drug MIC.

100, 107 and 114 were active under low oxygen conditions in combination with isoniaizid, by low oxygen recovery assay (LORA) (Table 3). All three 6-azasteroid INH mixtures showed decreased LORA MICs compared to that of isoniazid alone (>128 μM) (Cho, S. H. et al. 2007). This may due to potentiation of isoniazid potency by 6-azasteroid or the activity of 6-azasteroid alone under low oxygen conditions. In addition, the combination of 6-azasteroid and TB drug (isoniazid or bedaquiline, BDQ) is bactericidal at concentrations at which bactericidal activity is not observed with singular compound treatment. Bactericidal activity is important for sterilization of infection so to shorten the treatment time (Table 4).

TABLE 3

Low Oxygen Recovery Assay
Low Oxygen Recovery Assay LORA

| Compound mixture | MIC (μM) |
| --- | --- |
| INH | >128 |
| INH with 15 μM 100 | 0.75 |
| INH with 15 μM 107 | 0.75 |
| INH with 55 μM 114 | 2.75 |

TABLE 4

Bactericidal activity

| Compound mixture | MBC (μM) |
| --- | --- |
| 114 | >40 |
| INH | >230 |
| BDQ | 0.5 |
| INH with 13 μM 114 | 0.7 |
| BDQ with 10 μM 114 | 0.025 |
| INH with 12 μM 100 | 0.6 |
| INH with 60 μM 107 | 3 |

From the calculated MBC, the activity of 107 mixture was lower than that of the other two.

However, the time-kill curve of SB107: INH (FIG. 1) exhibited rapid killing during the first 14 days, at the concentration of SB107 at 12 μM. The re-growth of cells after day 14 indicates the generation of resistant bacteria or compound decomposition. There was no rapid killing in 15 days of Mtb with mono-treatment of 100 or 114 at the concentration range of 10-20 μM (FIG. 2), suggesting the rapid kill of the mixture is mainly due to the potentiation of azasteroid to isoniazid.

M. tuberculosis H37Rv cultures were exposed to compound mixtures for 21 days and cell viability measured by enumerating colony forming units (CFU) on agar plates on day 0, 7, 14 and 21 (FIG. 1).

Figure 2:
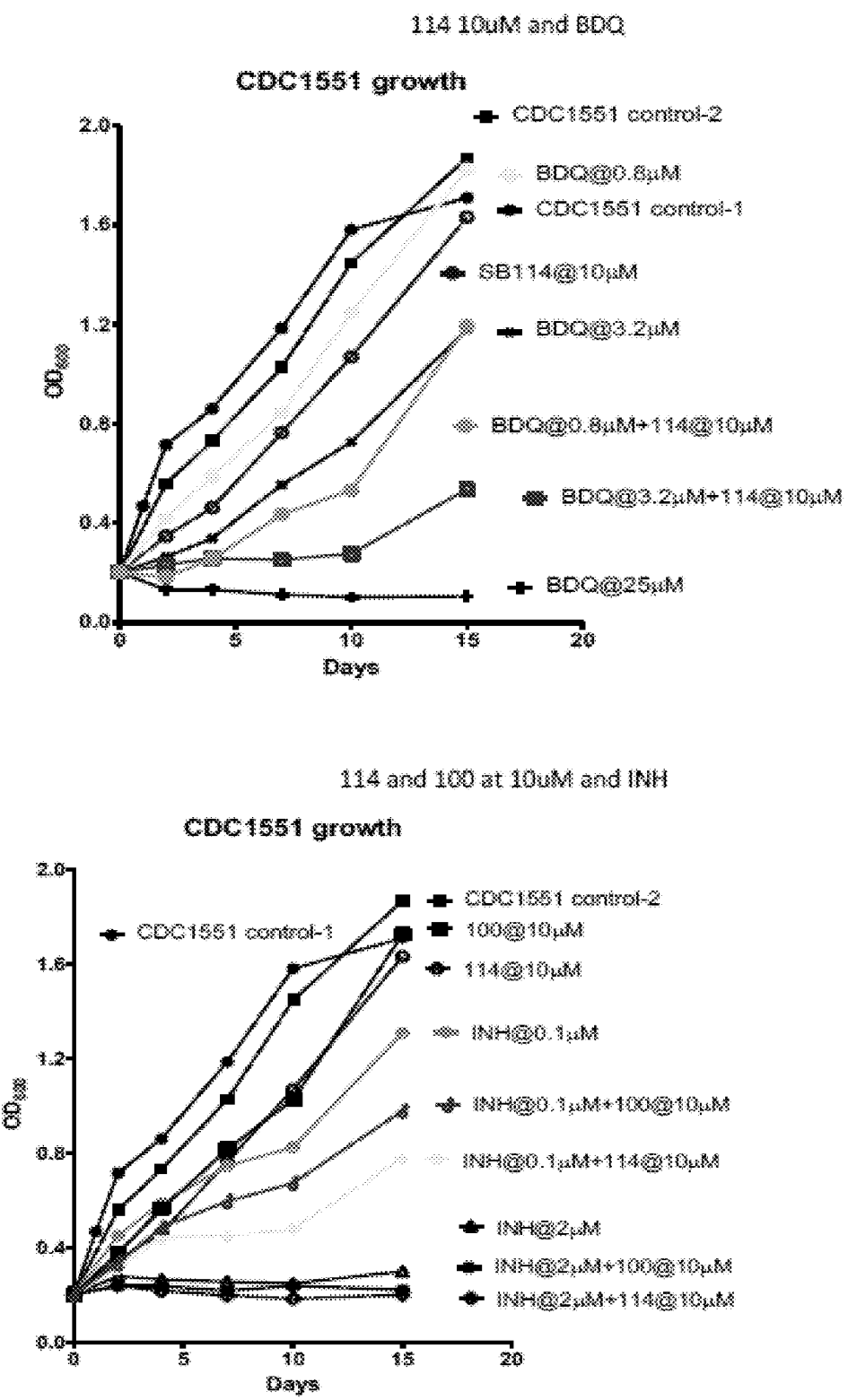
FIG. 2: *M. tuberculosis* CDC1551 in vitro kill kinetics.

Cells were incubated with (A) bedaquiline (BDQ) at selected concentrations with or without 10 μM SB114; (B) isoniazid (INH) at selected concentrations with or without 10 μM 100 or 114. Cell growth was monitored by optical density at 600 nm for 15 days (FIG. 2).

Figure 3:
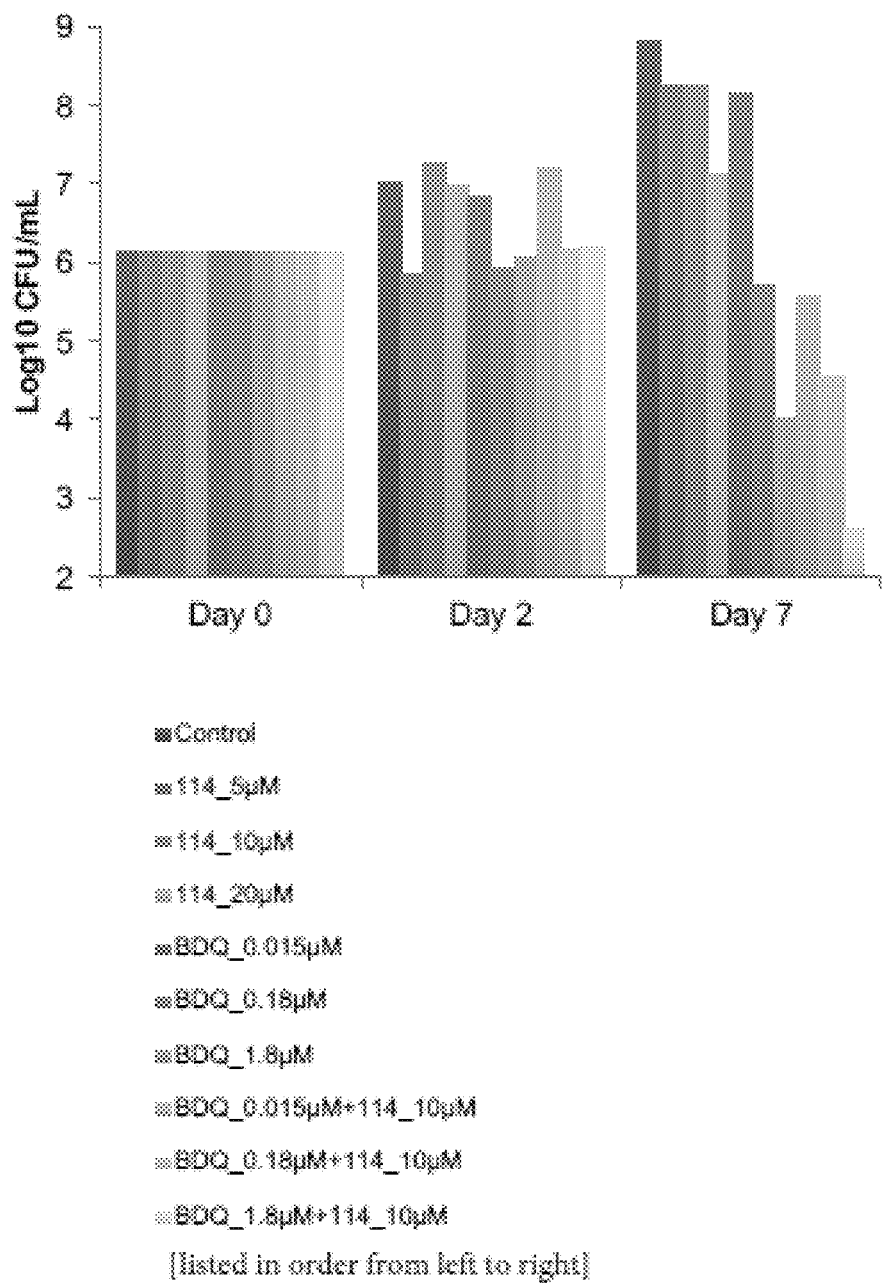
FIG. 3: Compound 114 improves bactericidal activity of bedaquiline (BDQ).

*M. tuberculosis* CDC1551 cells were incubated with 114 alone, bedaquiline alone or in combination. Cell viability was measured by enumerating colony forming units (CFU) on day 0, 2 and 7 (FIG. 3).

Example 4. Antibacterial Activity Against Mtb Resistant Isolates

The activity of compounds was assessed aerobically against five resistant isolates (Table 5). INH-R1 was derived from H37Rv and is a katG mutant (Y155*=truncation). INH-R2 (strain ATCC35822) was derived from H37Rv, containing alkyl hydroperoxide reductase C peptide (ahpC) promoter mutant (Wilson, T. M. et al. 1996). RIF-R1 was derived from H37Rv and is an rpoB mutant (S522L). RIF-R2 (ATCC35838) was derived from H37Rv. FQ-R1 is a fluoroquinolone-resistant strain derived from H37Rv and is a gyrA mutant (D94N).

TABLE 5

MICs against drug-resistant *M. tuberculosis* clinical strains.

| | MIC (μM) | | | | |
|---|---|---|---|---|---|
| Compound | FQ-R1 | INH-R1 | INH-R2 | RIF-R1 | RIF-R2 |
| 100:INH (20:1) | 12:0.6 | >200:>10 | >200:>10 | 6.6:0.33 | 12:0.6 |
| 107:INH (20:1) | 14:0.7 | >200:>10 | >200:>10 | 130.65 | 24:1.2 |
| 114:INH (20:1) | 13:0.65 | 78:3.9 | 65:3.3 | 6.9:3.5 | 14:0.7 |
| Rifampicin | 0.022 | 0.019 | 0.0063 | 6.2 | >50 |
| Isoniazid | 0.29 | >200 | >200 | 0.20 | 0.60 |
| Levofloxacin | 17 | 1.4 | 2.5 | 1.7 | 2.4 |

Example 5. In Vitro Evaluation of ADME Characteristics 100 is metabolically stable in in vitro incubations with human liver microsomes (Table 6 and 7). However, $T_{1/2}$ of 46.34 min in the current study is much shorter than the previously reported value 2.73 hr by Frye (Frye, S. V. 2006), which may due to different resources and activities of human liver microsomes used in the studies. 107 is the most stable one among all four 6-azasteroids tested.

TABLE 6

Metabolic stability of 6-azasteroids in human liver microsomes

| Compound | $T_{1/2}$ (min) | $CL_{int}$ (μL/min/mg protein) | Scaled-up $CL_{int}$ (mL/min/Kg) |
|---|---|---|---|
| 100 | 46.34 | 29.91 | 37.51 |
| 107 | 92.49 | 14.99 | 18.79 |
| 114 | 18.94 | 73.19 | NA |
| Verapamil | 15.13 | 91.60 | 114.88 |

TABLE 7

Metabolic stability of 6-azasteroids in human liver microsomes

| | Remaining Percentage (%) with NADPH | | | | |
|---|---|---|---|---|---|
| Compound | 0 min | 15 min | 30 min | 45 min | 60 min |
| Verapamil | 100.00 | 39.02 | 16.55 | 9.51 | 6.53 |
| 100 | 100.00 | 65.83 | 55.21 | 48.69 | 37.91 |
| 107 | 100.00 | 93.28 | 79.18 | 71.86 | 65.13 |
| 114 | 100.00 | 24.89 | 4.76 | 1.68 | 0.96 |

To predict absorption via oral administration, Caco-2 bidirectional permeability assay was performed (Table 8). The efflux ratios of SB100 and SB114 are around 0.5, indicating they are not a substrate for P-gp transporter. Papp(A-B) of 100 and 114 at 1.40 and $0.85 \times 10^{-6}$ suggests over 50% intestinal absorption (Zhao, Y. H. et al. 2001).

TABLE 8

Permeability of 6-azasteroids in Caco-2 cell line

| Compound | BSA (%) | $P_{app\,(A-B)}$ ($10^{-6}$, cm/s) | $P_{app\,(B-A)}$ ($10^{-6}$, cm/s) | Efflux Ratio | Recovery (%) AP-BL | Recovery (%) BL-AP |
|---|---|---|---|---|---|---|
| 100 | 0 | 1.32 | 1.70 | 1.28 | 17.21 | 27.55 |
| | 4 | 7.51 | 4.32 | 0.58 | 60.12 | 77.70 |
| 114 | 0 | 0.78 | 0.68 | 0.87 | 12.37 | 14.50 |
| | 4 | 8.36 | 4.03 | 0.48 | 64.77 | 71.94 |
| 107 | 0 | <0.05 | 0.05 | >1.06 | <71.79 | 63.36 |
| | 4 | 1.73 | 1.23 | 0.71 | 47.71 | 58.07 |

To predict the potential cardiotoxic effects of 6-azastroids, human ether-a-go-go related gene (hERG) assay was applied to 100, 107 and 114 (Table 9). Cytotoxicity of 107 was also assessed (Table 10).

TABLE 9

Inhibitory effects of 6-azasteroids on human hERG channel

| Compound | hERG IC$_{50}$ (μM) |
| --- | --- |
| 100 | 0.953 |
| 107 | >30* |
| 114 | 0.739 |
| Dofetilide | 0.012 |

*34.07% inhibition at 30 mM

TABLE 10

Cytotoxicity of 107

| Cell line | IC$_{50}$ (μM) |
| --- | --- |
| hERG | >30 |
| THP-1 | >30 |
| HepG-2 | >30 |
| HK-2 | >30 |

Example 6. Potential for Drug-Drug Interaction

The inhibition of CYP enzymes by 107 was evaluated in human liver microsomes (Table 11). 107 showed weak inhibition of CYP 3A4 with either midazolam or testosterone as a substrate with 107 at 10 μM (30% inhibition). The CYP 3A4 inhibition of 107 was further investigated in a separate study where the inhibition was tested with 107 from 10 nM to 50 μM with both substrates. 107 only showed weak inhibition of CYP 3A4 at 50 μM and the IC50s for both substrates are above 50 μM. SB107 showed weak or no inhibition of the rest of the CYPs tested, except CYP 2C19.

TABLE 11

Inhibition of Cytochrome P450s by SB107 (at 10 μM)

| Cytochrome P450 | % Inhibition |
| --- | --- |
| 1A2 | 0 |
| 2A6 | 16.5 |
| 2B6 | 0 |
| 2C8 | 39.7 |
| 2C9 | 33.1 |
| 2C19 | 65.3 |
| 2D6 | 4.4 |
| 2E1 | 0 |
| 3A4 (midazolam) | 30.4 |
| 3A4 (testosterone) | 30.5 |

Example 7: Pharmacokinetic (PK) and Bioavailability of 107

Mice were dosed intravenously (1 mg/kg) and orally (5 mg/kg) with SB107. After dosing, blood and lung samples were collected at different time points (5, 15, 30 min, 1, 2, 4, 6, 8 and 24 hours) for each group. Compound concentrations in plasma samples were analyzed by liquid chromatography-tandem mass spectrometry (LC-MS/MS). The bioavailability of 107 in the lung was 48% and the oral in vivo half life was 5.8 hours (Table 12).

TABLE 12

PK Parameters for 107

| PK parameters | Unit | Plasma | | Lung | |
| --- | --- | --- | --- | --- | --- |
| | | IV 1 mg/kg | PO 5 mg/kg | IV 1 mg/kg | PO 5 mg/kg |
| $t_{1/2}$ | h | 6.75 | 4.98 | 6.88 | 5.82 |
| $t_{max}$ | h | — | 1 | 0.0833 | 1 |
| $C_0$ ($C_{max}$) | ng/mL | 3762 | 640 | 2081 | 1075 |
| AUC$_{last}$ | h*ng/mL | 1330 | 2305 | 1686 | 4015 |
| AUC$_{Inf}$ | h*ng/mL | 1364 | 2361 | 1756 | 4172 |
| F | % | — | 34.6 | — | 47.5 |
| AUClast Ratio (Lung/Plasma) | NA | — | — | — | 1.74 |

Example 8. Frequency of Resistance

Resistant mutant formation with treatment of 114 alone or in combination with bedaquiline (Table 13). The frequency of BDQ resistance in vitro at 10×MIC is reported to be between $4.7 \times 10^{-7}$ and $8.9 \times 10^{-9}$ mutations per cell division, and mutations predominately arise in the atpE gene (Huitric, E. et al. 2010)

TABLE 13

In vitro frequencies of resistance

| Frequencies of resistance | BDQ 10 × MIC | BDQ 5 × MIC | BDQ none |
| --- | --- | --- | --- |
| 114 10 × MIC | $7.8 \times 10^{-8}$ | — | $1.1 \times 10^{-7}$ |
| 114 5 × MIC | — | $2 \times 10^{-7}$ | $3.6 \times 10^{-6}$ |
| 114 none | $5.5 \times 10^{-9}$ | $3.4 \times 10^{-7}$ | — |

Example 9. Intracellular Activity of SB 100

The activity of 100 was tested in combination with INH against intracellular bacteria in infected J774A.1 macrophage cell line. 100 at 20 μM improves the potency of INH 10-fold (Table 14).

TABLE 14

Intracellular activity of 100 in J774A.1 macrophages

| | 100 | INH only | INH with 100@20 uM |
| --- | --- | --- | --- |
| IC90 | >40 μM | >6 μM | ~1.5 μM |
| IC50 | 3 μM | ~1.5 μM | ~0.7 μM |

Example 10. Administration of 6-Azasteroids with Anti-TB Drug

An amount of compound 100 or 101 is administered in combination with an anti-tuberculosis drug to a subject infected with *M. tuberculosis*. The combination of the compound and drug is effective to treat the subject.

An amount of compound 100 or 101 is administered in combination with an anti-tuberculosis drug to a subject infected with *M. tuberculosis*. The combination of the compound and anti-tuberculosis drug is more effective to treat the subject than the anti-tuberculosis drug alone.

An amount of compound 100 or 101 is administered in combination with an anti-tuberculosis drug to a subject infected with *M. tuberculosis*. The compound is effective to enhance the therapeutic effect of the anti-tuberculosis drug.

An amount of any one of compounds 103-105, 107, 109 or 113-114 is administered in combination with an anti-tuberculosis drug to a subject infected with *M. tuberculosis*. The combination of the compound and drug is effective to treat the subject.

An amount of any one of compounds 103-105, 107, 109 or 113-114 is administered in combination with an anti-tuberculosis drug to a subject infected with *M. tuberculosis*. The combination of the compound and anti-tuberculosis drug is more effective to treat the subject than the anti-tuberculosis drug alone.

An amount of any one of compounds 103-105, 107, 109 or 113-114 is administered in combination with an anti-tuberculosis drug to a subject infected with *M. tuberculosis*. The compound is effective to enhance the therapeutic effect of the anti-tuberculosis drug.

Example 11. Administration of 6-Azasteroids with Isoniazid

An amount of compound 100 or 101 is administered in combination with isoniazid to a subject infected with *M. tuberculosis*. The combination of the compound and drug is effective to treat the subject.

An amount of compound 100 or 101 is administered in combination with isoniazid to a subject infected with *M. tuberculosis*. The combination of the compound and anti-tuberculosis drug is more effective to treat the subject than the anti-tuberculosis drug alone.

An amount of compound 100 or 101 is administered in combination with isoniazid to a subject infected with *M. tuberculosis*. The compound is effective to enhance the therapeutic effect of the anti-tuberculosis drug.

An amount of any one of compounds 103-105, 107, 109 or 113-114 is administered in combination with isoniazid to a subject infected with *M. tuberculosis*. The combination of the compound and drug is effective to treat the subject.

An amount of any one of compounds 103-105, 107, 109 or 13-114 is administered in combination with isoniazid to a subject infected with *M. tuberculosis*. The combination of the compound and anti-tuberculosis drug is more effective to treat the subject than the anti-tuberculosis drug alone.

An amount of any one of compounds 103-105, 107, 109 or 113-114 is administered in combination with isoniazid to a subject infected with *M. tuberculosis*. The compound is effective to enhance the therapeutic effect of the anti-tuberculosis drug.

Example 12. Administration of 6-Azasteroids with Ethionamide

An amount of compound 100 or 101 is administered in combination with ethionamide to a subject infected with *M. tuberculosis*. The combination of the compound and drug is effective to treat the subject.

An amount of compound 100 or 101 is administered in combination with ethionamide to a subject infected with *M. tuberculosis*. The combination of the compound and anti-tuberculosis drug is more effective to treat the subject than the anti-tuberculosis drug alone.

An amount of compound 100 or 101 is administered in combination with ethionamide to a subject infected with *M. tuberculosis*. The compound is effective to enhance the therapeutic effect of the anti-tuberculosis drug.

An amount of any one of compounds 100 or 101 is administered in combination with ethionamide to a subject infected with *M. tuberculosis*. The combination of the compound and drug is effective to treat the subject.

An amount of any one of compounds 103-105, 107, 109 or 113-114 is administered in combination with ethionamide to a subject infected with *M. tuberculosis*. The combination of the compound and anti-tuberculosis drug is more effective to treat the subject than the anti-tuberculosis drug alone.

An amount of any one of compounds 103-105, 107, 109 or 113-114 is administered in combination with ethionamide to a subject infected with *M. tuberculosis*. The compound is effective to enhance the therapeutic effect of the anti-tuberculosis drug.

Example 13. Administration of 6-Azasteroids with Bedaquiline

An amount of compound 100 or 101 is administered in combination with bedaquiline to a subject infected with *M. tuberculosis*. The combination of the compound and drug is effective to treat the subject.

An amount of compound 100 or 101 is administered in combination with bedaquiline to a subject infected with *M. tuberculosis*. The combination of the compound and anti-tuberculosis drug is more effective to treat the subject than the anti-tuberculosis drug alone.

An amount of compound 100 or 101 is administered in combination with bedaquiline to a subject infected with *M. tuberculosis*. The compound is effective to enhance the therapeutic effect of the anti-tuberculosis drug.

An amount of any one of compounds 100 or 101 is administered in combination with bedaquiline to a subject infected with *M. tuberculosis*. The combination of the compound and drug is effective to treat the subject.

An amount of any one of compounds 103-105, 107, 109 or 113-114 is administered in combination with bedaquiline to a subject infected with *M. tuberculosis*. The combination of the compound and anti-tuberculosis drug is more effective to treat the subject than the anti-tuberculosis drug alone.

An amount of any one of compounds 103-105, 107, 109 or 113-114 is administered in combination with bedaquiline to a subject infected with *M. tuberculosis*. The compound is effective to enhance the therapeutic effect of the anti-tuberculosis drug.

Example 14. Administration of 6-Azasteroids with Pretomanid

An amount of compound 100 or 101 is administered in combination with pretomanid to a subject infected with *M. tuberculosis*. The combination of the compound and drug is effective to treat the subject.

An amount of compound 100 or 101 is administered in combination with pretomanid to a subject infected with *M. tuberculosis*. The combination of the compound and anti-tuberculosis drug is more effective to treat the subject than the anti-tuberculosis drug alone.

An amount of compound 100 or 101 is administered in combination with pretomanid to a subject infected with *M. tuberculosis*. The compound is effective to enhance the therapeutic effect of the anti-tuberculosis drug.

An amount of any one of compounds 100 or 101 is administered in combination with pretomanid to a subject infected with *M. tuberculosis*. The combination of the compound and drug is effective to treat the subject.

An amount of any one of compounds 103-105, 107, 109 or 113-114 is administered in combination with pretomanid to a subject infected with *M. tuberculosis*. The combination of the compound and anti-tuberculosis drug is more effective to treat the subject than the anti-tuberculosis drug alone.

An amount of any one of compounds 103-105, 107, 109 or 113-114 is administered in combination with pretomanid to a subject infected with *M. tuberculosis*. The compound is effective to enhance the therapeutic effect of the anti-tuberculosis drug.

Example 15. Administration of 6-Azasteroids with Protionamide

An amount of compound 100 or 101 is administered in combination with protionamide to a subject infected with *M. tuberculosis*. The combination of the compound and drug is effective to treat the subject.

An amount of compound 100 or 101 is administered in combination with protionamide to a subject infected with *M. tuberculosis*. The combination of the compound and anti-tuberculosis drug is more effective to treat the subject than the anti-tuberculosis drug alone.

An amount of compound 100 or 101 is administered in combination with protionamide to a subject infected with *M. tuberculosis*. The compound is effective to enhance the therapeutic effect of the anti-tuberculosis drug.

An amount of any one of compounds 100 or 101 is administered in combination with protionamide to a subject infected with *M. tuberculosis*. The combination of the compound and drug is effective to treat the subject.

An amount of any one of compounds 103-105, 107, 109 or 113-114 is administered in combination with protionamide to a subject infected with *M. tuberculosis*. The combination of the compound and anti-tuberculosis drug is more effective to treat the subject than the anti-tuberculosis drug alone.

An amount of any one of compounds 103-105, 107, 109 or 113-114 is administered in combination with protionamide to a subject infected with *M. tuberculosis*. The compound is effective to enhance the therapeutic effect of the anti-tuberculosis drug.

Example 16. Administration of 6-Azasteroids with Second 6-Azasteroid

An amount of any one of compounds 100, 101, 103-105, 107, 109 or 113-114 is administered in combination with a different azasteroid compound of the present application and an anti-tuberculosis drug to a subject infected with *M. tuberculosis*. The combination of the compounds and drug is effective to treat the subject.

An amount of any one of compounds 100, 101, 103-105, 107, 109 or 113-114 is administered in combination with a different azasteroid compound of the present application and an anti-tuberculosis drug to a subject infected with *M. tuberculosis*. The combination of the compounds is more effective to treat the subject than either compound alone.

An amount of any one of compounds 100, 101, 103-105, 107, 109 or 113-114 is administered in combination with a different azasteroid compound of the present application and ethionamide or isoniazid to a subject infected with *M. tuberculosis*. The compounds and ethionamide or isoniazid is effective to enhance the therapeutic effect of the anti-tuberculosis drug.

Example 17. Additional Analogs

An additional aspect of the invention provides derivatives of compounds 100, 101, 103-105, 107, 109 or 113-114 that are active as anti-tuberculosis agents alone or in combination with an anti-tuberculosis drug. These derivatives have analogous or improved activity to any one of compounds 100, 101, 103-105, 107, 109 or 13-114.

DISCUSSION

*Mycobacterium tuberculosis* (Mtb), the causative agent of tuberculosis (TB) is estimated to infect 30% of the world's population (WHO 2011). There are 8.8 million new cases every year and 10% of Mtb infected individuals will develop active TB disease in their lifetime. The potential global market for anti-TB therapies is 200 million people worldwide. India, China, Indonesia, South Africa, and Nigeria have the world's highest TB incidence. South-east Asia accounts for ⅓ of new cases every year; Africa accounts for ⅓ of new TB cases every year and 20% of new TB cases are in China. The treatment success rates range from 51%-92% depending on region and health care infrastructure resulting in high rates of multidrug-resistant TB (MDR-TB) and extensively drug-resistant TB (XDR-TB). TB and HIV have high rates of co-infection, which increases the likelihood that an individual will develop active disease. TB rates are at unprecedented high levels in sub Saharan Africa (WHO 2019). For example, in South Africa, the estimated TB incidence rate is 1,000 per 100,000 population and 65% of TB patients are HIV coinfected (Kaiser Family Foundation 2009).

Within the US, there are about 10,000 cases of TB disease per year. The major risk factors for US citizens acquiring TB are two-fold. The first risk factor is from exposure to travelers from TB-endemic countries, either through exposure in the confines of long-haul air flights or upon extended household exposures by visitors (Grady, D. 2015a). Although infrequent, the TB is generally drug-resistant. A woman traveling from India visited three states over the course of 7 weeks before seeking treatment for what was diagnosed as extensively drug resistant TB. The US government is paid for her treatment (Grady, D. 2015b). Thus, treatments come at high public health cost, requiring widespread contact tracing and monitoring, in addition to treatment.

The second risk factor for TB disease is service in the United States Armed Services. US Service members are infected with Mtb upon deployment to host countries in which TB is endemic and US service members are in close contact with local populations. This type of exposure occurs upon active duty in disaster recovery operations, such as in Haiti (Pitchenik, A. E., et al. 1982; Kortepeter, M. G. et al. 2001) or upon prolonged stationing, e.g., in Korea (Mancuso, J. D. et al. 2010). Although TB is endemic in Iraq and Afghanistan, exposure to the general population is more limited, and the risk of Mtb infection is lower in these locales (Mancuso, J. D. et al. 2010).

The size of the US military is about 2.3 million active and reserve military and there are 22.7 million veterans. The second type of exposure occurs within the US armed services from foreign-born recruits. These recruits have latent TB from exposure in their birth countries (Mancuso, J. D. et al. 2010; Smith, B. et al. 2002). For example, in 2002, the rate of latent TB infection in U.S. Navy recruits was 3.5%, a 50% increase over the infection rate measured ten years previous. Foreign-born recruits were 8 times as likely to be infected, with even higher rates of infection observed in new recruits born in Africa and Central and South America.38 The stress of deployment and crowded living conditions of active-duty service members can lead to activation of latent infections and rapid transmission through a troop population.

Moreover, as of 2010, the National Quality Forum (NQF) estimates 20,000 United States Veterans are treated every year for HIV infection. The HIV status of these Veterans in combination with their previous global deployments and Mtb exposure puts this population at high risk for developing active TB later in life. The crowded conditions in which veterans often live also promote further transmission of active TB.

Thus, there is a large market for treatment of drug-sensitive, and drug-resistant TB disease, of about 9 million people; including latent TB the market increases to about 200 million. The biggest markets are primarily in developing countries. Due to global travel and deployment, there is significant need in the US for better TB treatments that minimize the public health cost that is incurred for the treatment of a few cases.

Total treatment costs for curing TB are high. Direct costs, which are almost entirely covered by the public sector are $134,000 for MDR-TB and $17,000 for drug-sensitive TB (Marks, S. M. et al. 2014). XDR-TB costs are estimated at $430,000 per treatment (Marks, S. M. et al. 2014). MDR-TB and XDR-TB costs are elevated due to required hospitalizations and isolations and the increased time for treatment. Thus, for every day of treatment time eliminated, between $100 and $200 are saved for the public health sector.

TB treatment in the US requires direct observation of therapy services (DOT) provided by a registered nurse (RN) or licensed practical nurse (LPN). The Current Procedural Terminology (CPT) code for a 15 min symptom and treatment monitoring session is 99212, and the reimbursement rate is ~$32-38 depending on geographic location, and whether at home or in a clinic (Marks, S. M. et al. 2014). Thus, ~$35 in nursing care is saved for each day treatment is shortened. DOT is required regardless of drug therapy due to public health concerns.

The drug costs for 6 months of isoniazid treatment for a drug-sensitive TB case is ~$30/patient (Marks, S. M. et al. 2014). The cost of isoniazid is primarily covered by the patient copay of between $0-$30 depending on the plan. The cost for two years of ethionamide treatment for an MDR-TB case is $9200/patient (Marks, S. M. et al. 2014). The insurer pays close to $9,000 for ethionamide, and the patient copay is about $250.

During the last 50 years, there is only one TB drug, bedaquiline, that has been approved by FDA. Bedaquiline is the most recent drug to come to market, and is the closest competitor for MDR-TB. Bedaquiline, introduced by Janssen was recently approved for treatment of MDR-TB and is priced at ~$30,000 for six months of therapy in insurer paying countries. It is estimated that even with this high pricing structure, the cost savings in the UK is approximately $18,000/patient (Wolfson, L. J., et al. 2015). This cost-benefit analysis is in spite of the black box warnings instituted by the FDA due to potentially increased rates of drug-induced mortality with bedaquiline compared to previous MDR-TB drug regimens (Cox, E. et al. 2014). The large infected population size combined with the multitude of drug-sensitive and drug-resistant forms of TB and the diversity of countries with endemic TB disease requires a multitude of new treatments to be available. Moreover, the toxicities of long-time TB drugs and new TB drugs leaves opening for drugs of lower toxicities.

Thus, new TB therapies are needed that reduce treatment time and have lower toxicities than existing drug regimens.

The 6-azasteroid scaffold (Thomas, S. T. et al. 2011) was originally developed as a 5α-reductase inhibitor (Frye, S. V. et al. 1993; Frye, S. V. et al. 1994; Frye, S. V. et al. 1995; Frye, S. V. et al. 2006). 6-azasteroid compounds were herein developed for treatment of TB, drug-sensitive TB and drug-resistant TB patients in combination with known TB drugs.

Compounds from this class reduce the MIC for front-line TB drug isoniazid from 400 nM to 6-25 nM with a co-MIC of 10-20 µM for the 6-azasteroids. The MICs for the 6-azasteroids alone are greater than 20 µM. The same effect is seen with bedaquiline. Thus, there is a synergistic effect between drugs. These compounds inhibit the first enzyme in the pathway, 3β-hydroxysteroid dehydrogenase, and show moderate inhibition of downstream enzymes in the pathway.

These 6-azasteroids compounds are orally available in mice. For example, 107 is 35% bioavailable in mice plasmae and is 48% bioavailable in mice lung at 5 mg/kg dosing. 107 has an in vivo serum half life at around 7 hours. No cytotoxicity was observed for 107 at 30 µM in THP-1, HepG-2 and HK-2 cells. No hERG inhibition was observed either for 107 at 30 µM. 100 and 101 were dosed to mice at 10 mg/kg by IP injection once per day, seven days per week, for 40 days, and no toxicity was observed.

One advantage of the present compounds is that in vitro they improve the potency of the required dose for isoniazid or bedaquiline, approved TB therapies. This reduction results in better toleration and shorter duration of isoniazid or bedaquiline therapy, which in turn reduces the incidence of drug resistance. In addition, improved potency of INH by use of the present compound facilitates the treatment of INH-resistant TB. Lastly, the present compound is active in the LORA assay which provides the advantage of treating latent or persistent infection.

The only more recent therapy for multidrug resistant TB, bedaqualine, was approved in late 2012 with a black box warning for increased mortality (Cox, E. et al. 2014) and it is administered with monitoring for cardio- and hepatotoxicity. Although it is not clear whether the increased mortality rates observed upon bedaquiline treatment are due to bedaqualine, it is clear that therapies with lower toxicities will have an advantage in the market. The preliminary toxicity of the 6-azasteroid testing with mice shows no toxicity with 10 mg/kg IP injection once per day, seven days a week, for 40 days.

In summary, 6-azasteroid compounds were identified that are useful to treat TB in combination with known TB drugs or other 6-azasteroid compounds.

REFERENCES

Andreu, N., et al. (2010) PLoS One 5, e10777.
Boshoff, H. I., et al. (2008) J. Biol. Chem. 283, 19329-41.
CDC. (2011) MMWR. 60, 1650-1653.
Chang, J. C., et al. (2009) J. Bacteriol. 191, 5232-9.
Cho, S. H., et al. (2007) Antimicrob Agents Chemother 51, 1380-1385.
Cox, E. and K. Laessig. (2014) N. Engl. J. Med. 371, 689-691.
De Voss, J. J., et al. (2000). Proc Natl Acad Sci USA 97, 1252-1257.
Editorial (2006) Lancet. 368, 964.
Frye, S. V., et al. (1993) J. Med. Chem. 36, 4313-5.
Frye, S. V., et al. (1994) J. Med. Chem. 37, 2352-60.
Frye, S. V., et al. (1995) J. Med. Chem. 38, 2621-7.
Frye, S. V. (2006) Curr Top Med Chem. 6, 405-21.

Grady, D. Tuberculosis Case Prompts Search for Patient's Fellow Airline Passengers. New York Times (2015a) Jun. 9, 2015, A8.

Grady, D. Indian Woman Being Treated in U.S. for Drug-Resistant Tuberculosis. New York Times (2015b) Jun. 10, 2015, A8.

Huitric, E., et al. (2010) Antimicrob. Agents Chemother. 54, 1022-1028.

Ioerger, T. R., et al. (2013) PLoS One 8, e75245.

Kaiser Family Foundation. The Global Tuberculosis Epidemic Fact Sheet. (2009).

Kortepeter, M. G. and M. R. Krauss. (2001) Military Med. 166, 116-20.

Kumar, A., et al. (2011) Expert Rev Mol Med. 13, e39.

Mancuso, J. D., et al. (2010) Am. J. Prev. Med. 39, 157-63.

Marks, S. M., et al. (2014) Emerg Infect Dis. 20, 812-21.

Murima, P., J. D. McKinney, and K. Pethe. (2014) Chem Biol. 21, 1423-32.

Nesbitt, N. M., et al. (2010) Infection Immun. 78, 275-282.

NIAID research agenda: Multidrug-resistant and extensively drug resistant tuberculosis, T. W. Group, Editor. 2007, NIAID: Bethesda, Md. p. 17.

Pandey, A. K. and C. M. Sassetti. (2008) Proc. Natl. Acad. Sci. U.S.A 105, 4376-80.

Pethe, K., et al. (2010) Nat. Commun. 1, 57.

Pitchenik, A. E., et al. (1982) N. Engl. J. Med. 307, 162-5.

Rasmusson, G. H., et al. (1984) J Med. Chem. 27(12), 1690-1701.

Rattan, A., A. Kalia, and N. Ahmad. (1998) Emerg. Infect. Dis. 4, 195-209.

Raviglione, M. C. and I. M. Smith. (2007) N. Engl. J. Med. 356, 656-9.

Rowland, K. (2012) Nature.

Russell, D. G., et al. (2009) Nat Immunol. 10, 943-8.

Schaefer, C., et al. (2015) Structure. 23, 21-33.

Smith, B., et al. (2002) Int. J. Epidemiol. 31, 934-9.

Suen, S. (2014) PLoS One. 2014; 9(3): e89822.

TB Alliance; Economic Impact. 2015

Thomas, S. T. et al. (2011) Bioorg Med Chem Lett. 2011 Apr. 15; 21(8): 2216-2219.

Vilcheze, C., et al. (2005) Antimicrob Agents Chemother. 49, 708-20.

Wakamoto, Y., et al. (2013) Science. 339, 91-5.

Wayne, L. G. (2001) Methods Mol Med 54, 247-269.

WHO Report. Global tuberculosis control—epidemiology, strategy, financing (2009).

WHO Report. Global Tuberculosis Control (2011).

WHO Report. Global tuberculosis control (2012).

Wilson, T. M., et al. (1996) *Mol Microbiol* 19, 1025-1034.

Wolfson, L. J., et al. (2015) PLoS ONE. 10, e0120763.

Yam, K. C., et al. (2009) PLoS Pathog. 5, e1000344.

Yang, X., et al. (2009) Biochemistry. 48, 3819-21.

Yang, M., et al. (2014) ACS Chemical Biology.

Yang, M., et al. (2015) ACS Infectious Disease. 1, 110-125.

Zhao, Y. H., et al. (2001) *J Pharm Sci* 90, 749-784.

What is claimed is:

1. A compound having the structure:

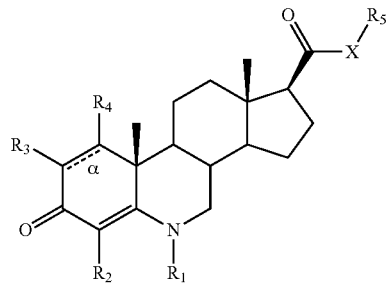

wherein

α is absent or present and when present is a bond,
  wherein when $R_3$ and $R_4$ combine to form a cycloalkyl group, then α is absent;

X is —NH—, —NH—NH—, —NH—C(O)—, —NH—C(S)—, —NH—NHC(O)— or —NH—NHC(S)—;

$R_1$ is —H, alkyl, alkenyl, alkynyl, aryl, C(O)-alkyl, C(O)-haloalkyl, C(O)-cycloalkyl, C(O)-alkenyl, C(O)-alkynyl, C(O)-aryl, $CO_2$-alkyl, $CO_2$-alkenyl, $CO_2$-alkynyl, $CO_2$-aryl, cycloalkyl, alkyl-OH, alkyl-$NH_2$, $SO_2$-alkyl, $SO_2$-haloalkyl, $SO_2$-cycloalkyl, $SO_2$-alkenyl, $SO_2$-alkynyl, $SO_2$-aryl, or L-(anti-tuberculosis drug),
  wherein the anti-tuberculosis drug is any one of isoniazid, ethionamide, pretomanid (PA-824), pyrazinamide, ethambutol, rifabutin, kanamycin, amikacin, capreomycin, streptomycin, levofloxacin, moxifloxacin, ofloxacin, para-aminosalicylic acid, cycloserine, terizidone, thionamide, protionamide, delamanid, bedaquiline, or rifampicin;

$R_2$ is H, halo, alkyl, alkenyl, alkynyl, aryl, $CO_2$-alkyl, $CO_2$-alkenyl, $CO_2$-alkynyl, $CO_2$-aryl, cycloalkyl, alkyl-OH, alkyl-$NH_2$ or alkyl-N(alkyl)$_2$;

$R_3$ is —H, halo, alkyl, alkenyl, alkynyl, aryl, $CO_2$-alkyl, $CO_2$-alkenyl, $CO_2$-alkynyl, $CO_2$-aryl, cycloalkyl, alkyl-OH, alkyl-$NH_2$ or alkyl-N(alkyl)$_2$, and $R_4$ is —H, halo, alkyl, alkenyl, alkynyl, aryl, $CO_2$-alkyl, $CO_2$-alkenyl, $CO_2$-alkynyl, $CO_2$-aryl, cycloalkyl, alkyl-OH, alkyl-$NH_2$, or alkyl-N(alkyl)$_2$, or $R_3$ and $R_4$ combine to form a cycloalkyl group;

$R_5$ is a substituted pyridyl
  wherein the substituted pyridyl is substituted with halo, —CN, —$CF_3$, —$OCF_3$, -alkyl, -alkenyl, -alkynyl, -aryl, -heteroaryl, —$NH_2$, —NH-alkyl, —NH-alkenyl, —NH-alkynyl, —NH-aryl, —NH-heteroaryl, —OH, —OAc, —O—C(O)alkyl, —O-alkyl, —O-alkylaryl, —O-alkenyl, —O-alkynyl, —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), —$SO_2$-(heteroaryl), alkyl-OH, alkyl-O-alkyl, alkyl-$NH_2$, alkyl-NH-alkyl, alkyl-N(alkyl)$_2$, cycloalkyl or alkyl-cycloalkyl, wherein L is a chemical linker comprising a functional group capable of forming a bond with an anti-tuberculosis drug;

or a salt thereof.

2. The compound of claim 1 having the structure:

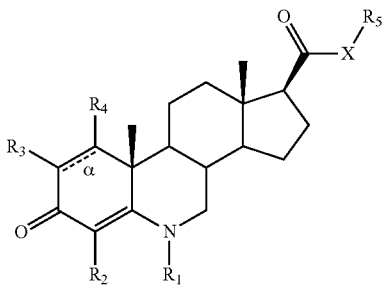

wherein
α is absent or present and when present is a bond,
   wherein when $R_3$ and $R_4$ combine to form a cycloalkyl group, then α is absent;
X is —NH—, —NH—NH—, —NH—C(O)—, —NH—C(S)—, —NH—NHC(O)— or —NH—NHC(S)—;
$R_1$ is —H, alkyl, alkenyl, alkynyl, aryl, $CO_2$-alkyl, $CO_2$-alkenyl, $CO_2$-alkynyl, $CO_2$-aryl, cycloalkyl, alkyl-OH, alkyl-$NH_2$, or L-(anti-tuberculosis drug),
   wherein the anti-tuberculosis drug is any one of isoniazid, ethionamide, pretomanid (PA-824), pyrazinamide, ethambutol, rifabutin, kanamycin, amikacin, capreomycin, streptomycin, levofloxacin, moxifloxacin, ofloxacin, para-aminosalicylic acid, cycloserine, terizidone, thionamide, protionamide, delamanid, bedaquiline, or rifampicin;
$R_2$ is H, halo, alkyl, alkenyl, alkynyl, aryl, $CO_2$-alkyl, $CO_2$-alkenyl, $CO_2$-alkynyl, $CO_2$-aryl, cycloalkyl, alkyl-OH, alkyl-$NH_2$ or alkyl-N(alkyl)$_2$;
$R_3$ is —H, halo, alkyl, alkenyl, alkynyl, aryl, $CO_2$-alkyl, $CO_2$-alkenyl, $CO_2$-alkynyl, $CO_2$-aryl, cycloalkyl, alkyl-OH, alkyl-$NH_2$ or alkyl-N(alkyl)$_2$, and
$R_4$ is —H, halo, alkyl, alkenyl, alkynyl, aryl, $CO_2$-alkyl, $CO_2$-alkenyl, $CO_2$-alkynyl, $CO_2$-aryl, cycloalkyl, alkyl-OH, alkyl-$NH_2$, or alkyl-N(alkyl)$_2$, or
$R_3$ and $R_4$ combine to form a cycloalkyl group;
$R_5$ is a substituted pyridyl
   wherein the substituted pyridyl is substituted with halo, —CN, —$CF_3$, —$OCF_3$, -alkyl, -alkenyl, -alkynyl, -aryl, -heteroaryl, —$NH_2$, —NH-alkyl, —NH-alkenyl, —NH-alkynyl, —NH-aryl, —NH-heteroaryl, —OH, —OAc, —O—C(O)alkyl, —O-alkyl, —O-alkylaryl, —O-alkenyl, —O-alkynyl, —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), —$SO_2$-(heteroaryl), alkyl-OH, alkyl-O-alkyl, alkyl-$NH_2$, alkyl-NH-alkyl, alkyl-N(alkyl)$_2$, cycloalkyl or alkyl-cycloalkyl,
wherein L is a chemical linker comprising a functional group capable of forming a bond with an anti-tuberculosis drug;
or a salt thereof.

3. The compound of claim 1,
wherein
α is absent or present and when present is a bond,
   wherein when $R_3$ and $R_4$ combine to form a cycloalkyl group, then α is absent;
X is —NH—;
$R_1$ is —H, alkyl, alkenyl, alkynyl, aryl, C(O)-alkyl, C(O)-haloalkyl, C(O)-cycloalkyl, C(O)-alkenyl, C(O)-alkynyl, C(O)-aryl, $CO_2$-alkyl, $CO_2$-alkenyl, $CO_2$-alkynyl, $CO_2$-aryl, cycloalkyl, alkyl-OH, alkyl-$NH_2$, $SO_2$-alkyl, $SO_2$-haloalkyl, $SO_2$-cycloalkyl, $SO_2$-alkenyl, $SO_2$-alkynyl, $SO_2$-aryl,
$R_2$ is H, halo, alkyl, alkenyl, alkynyl, aryl, $CO_2$-alkyl, $CO_2$-alkenyl, $CO_2$-alkynyl, $CO_2$-aryl, cycloalkyl, alkyl-OH, alkyl-$NH_2$ or alkyl-N(alkyl)$_2$;
$R_3$ is —H, halo, alkyl, alkenyl, alkynyl, aryl, $CO_2$-alkyl, $CO_2$-alkenyl, $CO_2$-alkynyl, $CO_2$-aryl, cycloalkyl, alkyl-OH, alkyl-$NH_2$ or alkyl-N(alkyl)$_2$, and
$R_4$ is —H, halo, alkyl, alkenyl, alkynyl, aryl, $CO_2$-alkyl, $CO_2$-alkenyl, $CO_2$-alkynyl, $CO_2$-aryl, cycloalkyl, alkyl-OH, alkyl-$NH_2$, or alkyl-N(alkyl)$_2$, or
$R_3$ and $R_4$ combine to form a cycloalkyl group;
$R_5$ is a substituted pyridyl
   wherein the substituted pyridyl is substituted with halo, —CN, —$CF_3$, —$OCF_3$, -alkyl, -alkenyl, -alkynyl, -aryl, -heteroaryl, —$NH_2$, —NH-alkyl, —NH-alkenyl, —NH-alkynyl, —NH-aryl, —NH-heteroaryl, —OH, —OAc, —O—C(O)alkyl, —O-alkyl, —O-alkylaryl, —O-alkenyl, —O-alkynyl, —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —$SO_2$-(alkyl), —$SO_2$-(aryl), —$SO_2$-(heteroaryl), alkyl-OH, alkyl-O-alkyl, alkyl-$NH_2$, alkyl-NH-alkyl, alkyl-N(alkyl)$_2$, cycloalkyl or alkyl-cycloalkyl,
or a salt thereof.

4. The compound of claim 1, wherein the alkyl group in $R_1$, $R_2$, $R_3$, $R_4$, and $R_5$ is a t-butyl group.

5. The compound of claim 1, wherein $R_5$ is

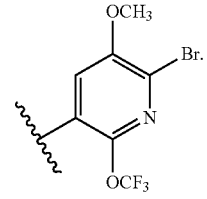 [SMILES: *c1cc(OC)c(Br)nc1OC(F)(F)F]

6. The compound of claim 1, wherein $R_5$ is

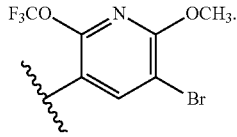

7. The compound of claim 1, wherein the pyridyl in $R_5$ is trisubstituted.

8. The compound of claim 1, wherein $R_5$ has the structure:

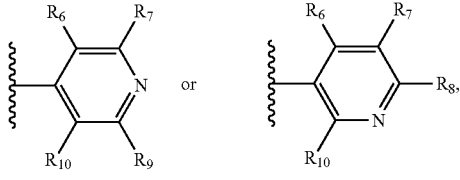

wherein $R_6$, $R_7$, $R_8$, $R_9$ and $R_{10}$ are each, independently, —H, halo, —CN, —$CF_3$, —$OCF_3$, -alkyl, -alkenyl, -alkynyl, -aryl, —$NH_2$, —NH-alkyl, —NH-alkenyl, —NH-alkynyl, —NH-aryl, —OH, —OAc, —O—C(O)alkyl, —O-alkyl, —O-alkylaryl, —O-alkenyl, —O-alkynyl, —O-(aryl), —S-(alkyl), —S-(alkenyl), —S-(alkynyl), —S-(aryl), —S(O)-(alkyl), —S(O)-(aryl), —SO$_2$-(alkyl), —SO$_2$-(aryl), alkyl-OH, alkyl-O-alkyl, alkyl-NH$_2$, alkyl-NH-alkyl, alkyl-N(alkyl)$_2$, cycloalkyl or alkyl-cycloalkyl.

9. The compound of claim 8, wherein R$_5$ has the structure:

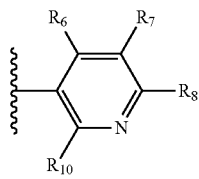

wherein R$_7$, R$_8$ and R$_{10}$ are each, independently, halo, —CN, —CF$_3$, —OCF$_3$, -alkyl, -alkenyl, -alkynyl, -aryl, —NH$_2$, —NH-alkyl, —NH-alkenyl, —NH-alkynyl, —NH-aryl, —OH, —OAc, —O—C(O)alkyl, —O-alkyl, —O-alkylaryl, —O-alkenyl, —O-alkynyl, —O-(aryl), —S-(alkyl), —S-(alkenyl), —S-(alkynyl), —S-(aryl), —S(O)-(alkyl), —S(O)-(aryl), —SO$_2$-(alkyl), —SO$_2$-(aryl), alkyl-OH, alkyl-O-alkyl, alkyl-NH$_2$, alkyl-NH-alkyl, alkyl-N(alkyl)$_2$, cycloalkyl or alkyl-cycloalkyl; and R$_6$ is —H.

10. The compound of claim 1, wherein R$_1$ is H, alkyl, or CO$_2$-alkyl.

11. The compound of claim 1, wherein R$_2$ is H, alkyl, cycloalkyl or alkyl-N(alkyl)$_2$.

12. The compound of claim 1, wherein R$_3$ is H or alkyl, and/or R$_4$ is H or alkyl.

13. The compound of claim 1, wherein R$_1$, R$_2$, R$_3$ and R$_4$ are each —H.

14. The compound of claim 1 having the structure:

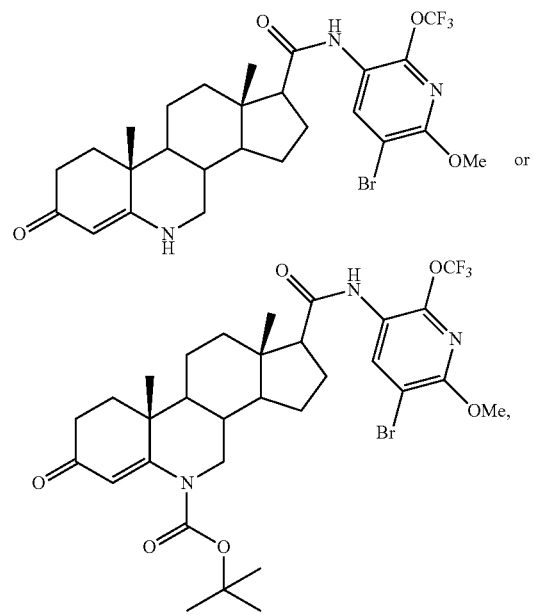

or a salt thereof.

15. A pharmaceutical composition comprising the compound of claim 1 and a pharmaceutically acceptable carrier, and optimally any one of the anti-tuberculosis drugs isoniazid or ethionamide.

16. A method of treating a subject infected with *M. tuberculosis* comprising administering to the subject an amount of the compound of claim 1 so as to thereby treat the subject.

17. A method of treating a subject infected with *M. tuberculosis* comprising administering to the subject an amount of the compound having the structure:

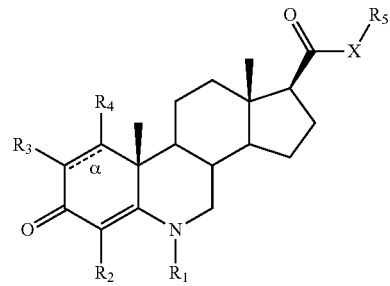

wherein

α is absent or present and when present is a bond, wherein when R$_3$ and R$_4$ combine to form a cycloalkyl group, then α is absent;

X is —NH—, —NH—NH—, —NH—C(O)—, —NH—C(S)—, —NH—NHC(O)— or —NH—NHC(S)—;

R$_1$ is —H, alkyl, alkenyl, alkynyl, aryl, C(O)-alkyl, C(O)-haloalkyl, C(O)-cycloalkyl, C(O)-alkenyl, C(O)-alkynyl, C(O)-aryl, CO$_2$-alkyl, CO$_2$-alkenyl, CO$_2$-alkynyl, CO$_2$-aryl, cycloalkyl, alkyl-OH, alkyl-NH$_2$, SO$_2$-alkyl, SO$_2$-haloalkyl, SO$_2$-cycloalkyl, SO$_2$-alkenyl, SO$_2$-alkynyl, SO$_2$-aryl, or L-(anti-tuberculosis drug), wherein the anti-tuberculosis drug is any one of isoniazid, ethionamide, pretomanid (PA-824), pyrazinamide, ethambutol, rifabutin, kanamycin, amikacin, capreomycin, streptomycin, levofloxacin, moxifloxacin, ofloxacin, para-aminosalicylic acid, cycloserine, terizidone, thionamide, protionamide, delamanid, bedaquiline, or rifampicin;

R$_2$ is H, halo, alkyl, alkenyl, alkynyl, aryl, CO$_2$-alkyl, CO$_2$-alkenyl, CO$_2$-alkynyl, CO$_2$-aryl, cycloalkyl, alkyl-OH, alkyl-NH$_2$ or alkyl-N(alkyl)$_2$;

R$_3$ is —H, halo, alkyl, alkenyl, alkynyl, aryl, CO$_2$-alkyl, CO$_2$-alkenyl, CO$_2$-alkynyl, CO$_2$-aryl, cycloalkyl, alkyl-OH, alkyl-NH$_2$ or alkyl-N(alkyl)$_2$, and R$_4$ is —H, halo, alkyl, alkenyl, alkynyl, aryl, CO$_2$-alkyl, CO$_2$-alkenyl, CO$_2$-alkynyl, CO$_2$-aryl, cycloalkyl, alkyl-OH, alkyl-NH$_2$, or alkyl-N(alkyl)$_2$, or R$_3$ and R$_4$ combine to form a cycloalkyl group;

R$_5$ is a substituted pyridyl wherein the substituted pyridyl is substituted with halo, —CN, —CF$_3$, —OCF$_3$, -alkyl, -alkenyl, -alkynyl, -aryl, -heteroaryl, —NH$_2$, —NH-alkyl, —NH-alkenyl, —NH-alkynyl, —NH-aryl, —NH-heteroaryl, —OH, —OAc, —O—C(O)alkyl, —O-alkyl, —O-alkylaryl, —O-alkenyl, —O-alkynyl, —O-(aryl), —O-(heteroaryl), —S-(alkyl), —S-(alkenyl), —S-(alkynyl), —S-(aryl), —S-(heteroaryl), —S(O)-(alkyl), —S(O)-(aryl), —S(O)-(heteroaryl), —SO$_2$-(alkyl), —SO$_2$-(aryl), —SO$_2$-(heteroaryl), alkyl-OH, alkyl-O-alkyl, alkyl-NH$_2$, alkyl-NH-alkyl, alkyl-N(alkyl)$_2$, cycloalkyl or alkyl-cycloalkyl;

when α is absent, X is NH, $R_1$ is H or Boc, and $R_2$, $R_3$ and $R_4$ are each H, then $R_5$ is other than 6-(5-fluoro-indol-1-yl)-2-(trifluoromethoxy)pyridin-3-yl, and when α is absent, X is —NH—C(S)—, and $R_1$, $R_2$, $R_3$ and $R_4$ are each H, then $R_5$ is other than 2-ethylpyridin-4-yl, or a salt thereof, in combination with an anti-tuberculosis drug, so as to thereby treat the subject, wherein the anti-tuberculosis drug is any one of isoniazid, ethionamide, pretomanid (PA-824), pyrazinamide, ethambutol, rifabutin, kanamycin, amikacin, capreomycin, streptomycin, levofloxacin, moxifloxacin, ofloxacin, para-aminosalicylic acid, cycloserine, terizidone, thionamide, protionamide, delamanid, bedaquiline, or rifampicin.

18. A pharmaceutical composition comprising the compound of claim 1, a pharmaceutically acceptable carrier, and an anti-tuberculosis drug, wherein the compound enhances the effect of the anti-tuberculosis drug.

19. The compound of claim 1, wherein at least two alkyl groups in $R_1$, $R_2$, $R_3$, $R_4$, and $R_5$ are t-butyl groups.

* * * * *